US011441174B2

(12) United States Patent
Shapero et al.

(10) Patent No.: US 11,441,174 B2
(45) Date of Patent: Sep. 13, 2022

(54) ARRAY-BASED METHODS FOR ANALYSING MIXED SAMPLES USING DIFFERENTLY LABELLED ALLELE-SPECIFIC PROBES

(71) Applicant: AFFYMETRIX, INC., Carlsbad, CA (US)

(72) Inventors: Michael Shapero, Campbell, CA (US); Ronald Sapolsky, Palo Alto, CA (US); Eric Fung, Los Altos, CA (US); Jeanette Schmidt, Palo Alto, CA (US); Monica Chadha, Fremont, CA (US); Anju Shukla, San Jose, CA (US)

( * ) Notice: Subject to any disclaimer, the term of this patent is extended or adjusted under 35 U.S.C. 154(b) by 172 days.

(21) Appl. No.: 16/616,741

(22) PCT Filed: Jun. 1, 2018

(86) PCT No.: PCT/US2018/035684
§ 371 (c)(1),
(2) Date: Nov. 25, 2019

(87) PCT Pub. No.: WO2018/223053
PCT Pub. Date: Dec. 6, 2018

(65) Prior Publication Data
US 2021/0147920 A1 May 20, 2021

Related U.S. Application Data

(60) Provisional application No. 62/514,629, filed on Jun. 2, 2017.

(51) Int. Cl.
*C12Q 1/6837* (2018.01)
*C12Q 1/6827* (2018.01)

(52) U.S. Cl.
CPC ......... *C12Q 1/6837* (2013.01); *C12Q 1/6827* (2013.01); *C12Q 2535/131* (2013.01); *C12Q 2537/125* (2013.01); *C12Q 2537/143* (2013.01)

(58) Field of Classification Search
None
See application file for complete search history.

(56) References Cited

U.S. PATENT DOCUMENTS

| 6,534,293 B1 | 3/2003 | Barany et al. |
| 2011/0029251 A1 | 2/2011 | Huang et al. |
| 2013/0059733 A1 | 3/2013 | Lo et al. |

FOREIGN PATENT DOCUMENTS

| WO | WO-2007147079 A2 | 12/2007 |
| WO | WO-2015154028 A1 | 10/2015 |
| WO | WO-2016018986 A1 | 2/2016 |
| WO | WO-2017020023 A2 | 2/2017 |
| WO | WO-2017205827 A1 | 11/2017 |

OTHER PUBLICATIONS

Wang, Y. et al., High quality copy number and genotype data from FFPE samples using Molecular Inversion Probe (MIP) microarrays, BMC Med. Genomics, vol. 2:8, pp. 1-13 (Year: 2009).*
Fan J-B, et al., "Highly Parallel SNP Genotyping," Cold Spring Harbor Symposia on Quantitative Biology, vol. 68, Jan. 1, 2003 (Jan. 1, 2003), pp. 69-78, XP001538040, DOI: 10.1101/SQB.2003.68.69.
Gunderson K.L, et al., "A Genome-Wide Scalable SNP Genotyping Assay Using Microarray Technology," Nature Genetics, vol. 37, No. 5, May 1, 2005 (May 1, 2005), pp. 549-554, XP002561532, DOI: 10.1038/NG1547.
Nicolaides K.H, et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, vol. 33, No. 6, Jun. 24, 2013 (Jun. 24, 2013), pp. 575-579, XP055257233, DOI: 10.1002/pd.4103.
PCT/US2018/035684, Preliminary Report on Patentability, dated Dec. 12, 2019.
PCT/US2018/035684, Search Report and Written Opinion, dated Aug. 3, 2018, 12 pages.
PCT/US2018/035686, Preliminary Report on Patentability, dated Dec. 12, 2019.
PCT/US2018/035686, Search Report and Written Opinion, dated Aug. 3, 2018, 13 pages.
PCT/US2018/035688, Preliminary Report on Patentability, dated Dec. 12, 2019.
PCT/US2018/035688, Search Report and Written Opinion, dated Aug. 2, 2018, 10 pages.
Zhang H, et al., "Statistical Approach to Decreasing the Error Rate of Noninvasive Prenatal Aneuploid Detection Caused by Maternal Copy Number Variation", Scientific Reports, vol. 5, No. 1, Nov. 4, 2015 (Nov. 4, 2015), pp. 1-9, XP055407852, DOI: 10.1038/srep16106.
Affymetrix "Genotyping Console 4.0," User Manual, 2009, pp. 1-327.
Affymetrix white paper "DMET™ Plus Genotyping and copy number methods," 2011, pp. 1-29.

(Continued)

*Primary Examiner* — Teresa E Strzelecka
(74) *Attorney, Agent, or Firm* — Workman Nydegger; Logan Christenson; John Guynn

(57) ABSTRACT

This disclosure provides methods and kits useful in analysis of mixed nucleic acid populations, including for multiplex genotyping of a mixed nucleic acid sample and for detecting differences in copy number of a target polynucleotide and/or a target chromosome (e.g., microdeletions, duplications and aneuploidies). The disclosure also provides methods and systems useful in the diagnosis of genetic abnormalities in a mixed nucleic acid population taken non-invasively from an organism, such as a sample of blood, plasma, serum, urine stool or saliva. The disclosed methods and systems find use in multiple applications, including prenatal testing and cancer diagnostics. The method is based on the hybridisation of amplified fragments obtained from the sample, e.g. using molecular inversion probes (MIP) to an oligonucleotide array and the detection of the alleles based on different signals from the different alleles of the SNP.

18 Claims, 4 Drawing Sheets

(56) References Cited

OTHER PUBLICATIONS

Attiyeh E.F., et al., "Genomic Copy number Determination in Cancer Cells From Single Nucleotide Polymorphism Microarrays Based on Quantitative Genotyping Corrected for Aneuploidy," Genome Research, 2009, vol. 19, pp. 276-283.

Juneau K., et al., "Microarray-Based Cell-Free DNA Analysis Improves Noninvasive Prenatal Testing," Fetal Diagnosis and Therapy, 2014, vol. 36, pp. 282-286.

Huang M.C., et al., "An Integrated Analysis Tool for Analyzing Hybridization Intensities and Genotypes Using New-Generation Population-Optimized Human Arrays," BMC Genomics, 2016, vol. 17:266, pp. 1-30.

\* cited by examiner

ARRAY-BASED METHODS FOR ANALYSING MIXED SAMPLES USING DIFFERENTLY LABELLED ALLELE-SPECIFIC PROBES

RELATED APPLICATIONS

This application is a U.S. 371 application of International Application No. PCT/US2018/035684, filed Jun. 1, 2018, which claims priority from U.S. Provisional patent application No. 62/514,629, filed Jun. 2, 2017, which is hereby incorporated herein by reference in its entirety for all purposes.

TECHNICAL FIELD

This disclosure provides methods and systems useful in array-based analysis of mixed nucleic acid populations, including for genotyping and copy number analysis of the various subpopulations of the mixed nucleic acid population. The disclosure also provides methods and systems useful in the diagnosis of genetic abnormalities in a mixed nucleic acid population taken from an organism. For example, disclosed herein are methods and systems useful in the diagnosis of fetal genetic abnormalities or tumor genetic abnormalities using samples obtained noninvasively from pregnant females or patients. Such samples can include mixed nucleic acid populations derived from blood, plasma, serum, urine, stool or saliva.

BACKGROUND

Analysis of mixed nucleic acid populations, for example DNA and RNA samples obtained from a single tissue source such as blood, urine or saliva but containing distinct nucleic acid subpopulations, has elicited significant interest in the research and health care communities. Using suitable methods, mixed nucleic acid populations derived from cell-free DNA (or RNA) taken from pregnant females can be analyzed to determine fetal characteristics, including disease inheritance. Similarly, mixed nucleic acid populations derived from cell-free DNA (or RNA) taken from cancer patients can be analyzed to determine various characteristics such as tumor malignancy, tumor origin or drug susceptibility. While analysis of such mixed nucleic acid populations can be technically complex due to the high degree of similarity between the various subpopulations, the difficulty of the analysis is outweighed by the ease of obtaining appropriate nucleic acid samples cheaply, quickly and noninvasively through procedures such as phlebotomy or urine/saliva collection. One mode of analyzing cell-free DNA, nucleic acid sequencing, is informative but costly on a per-sample and time-consuming Microarray analysis is cheaper and quicker than sequencing, but current commercial embodiments of microarray products do not readily support discrimination between the different and highly similar subpopulations present in a mixed nucleic acid population. As a result of the low concentration of fetal DNA in maternal samples, and low concentration of tumor DNA in a blood sample containing circulating tumor cells, single or low multiplex assays are unlikely to differentiate between an aneuploid fetus (e.g., trisomy of chromosome 21) from a euploid fetus, or a tumor cell from a healthy cell in a cancer patient. For example, fetal DNA can be present at levels of between 4%-15% of total cell-free DNA in blood; DNA derived from a particular fetal chromosome would represent one-twenty-third of such fetal DNA. Detection of a trisomy would require reliable detection of signal changes as low as 1-2% above background. Moreover, the analysis is further complicated by the limited amount of nucleic acid available through non-invasive sampling methods. For example, a maternal sample of 10 mls of whole blood can yield between 5 and 15 ng of purified cell-free DNA in a typical assay.

Due to the current challenges posed by such non-invasive approaches, a majority of pregnant women are subject to prenatal testing, including maternal serum screening and/or an ultrasound test, to determine risks for common birth defects, such as those resulting from trisomy 13, 18, and 21. However, the sensitivity and specificity of such tests are very poor leading to high false positive rates. As a result of the high false positive rates of such conventional tests, individuals typically must conduct follow-up testing with an invasive diagnostic test, such as Chorionic Villus Sampling (CVS) between 11 and 14 weeks gestation or amniocentesis after 15 weeks gestation. These invasive procedures carry a risk of a miscarriage of around one percent (see Mujezinovic and Alfirevic, Obstet. Gynecol., 110:687-694 (2011)). Current analysis of fetal cells typically involves karyotyping or fluorescent in situ hybridization (FISH) and does not provide information about single gene traits. As a result, additional tests are required for identification of single gene diseases and disorders. Because prenatal diagnosis can be critical for management of a pregnancy with chromosomal abnormalities and localized genetic abnormalities, an accurate and early diagnosis is important to allow for interventional care before or during delivery and to prevent devastating consequences for the neonate.

Similarly, on the cancer front, powerful tools such as OncoScan® have been developed for purposes of diagnosing cancers. However, such samples are typically biopsy samples taken in invasive procedures that are both expensive and potentially risky to the patient. Through the use of microarray-based technology, researchers are able to identify large numbers of Single Nucleotide Polymorphisms (SNPs) on a single array, which allows for the rapid and accurate detection of genetic abnormalities in a subject. As an example of one such product is the SNP detection microarray product from Affymetrix called OncoScan®. The OncoScan® product provides genome-wide copy number and loss-of-heterozygosity (LOH) profiles from solid tumor samples. Such a technology is a powerful tool in cancer diagnostics because it helps to overcome significant challenge due to the difficulty of working with limited amounts of DNA from highly degraded FFPE samples. See, for example, U.S. Pat. No. 8,190,373. However, such technologies are finding application in numerous other fields, as well. Specifically, genetic abnormalities account for a wide number of pathologies, including pathologies caused by chromosomal aneuploidy (e.g., Down syndrome), germline mutations in specific genes (e.g., sickle cell anemia), and pathologies caused by somatic mutations (e.g., cancer), and in many cases, the detection of such genetic abnormalities is complicated by invasive diagnostic procedures.

As such, the development of a microarray based test that is sensitive and specific enough to detect genetic abnormalities in samples of mixed nucleic acid populations obtained by non-invasive means with low false-positive and false-negative rates would be of benefit to the field of molecular diagnostics. Recently, Ariosa Diagnostics reported studies involving microarray based analysis of cell-free DNA from maternal blood to detect the presence of fetal aneuploidies. See, e.g., Stokowski et al., Prenatal Diagnosis 35:1243-1246 (2015). Such methods involved analysis of bulk signals from non-polymorphic loci (i.e., loci that are expected to be identical for both mother and fetus) to estimate chromosomal copy number by simply measuring fluctuations in total signal detected from both maternal and fetal DNA at a given genetic locus. This necessitates a design strategy whereby the array is configured to interrogate non-polymorphic loci to determine copy number of the underlying chromosomes. There is a need to develop improved methods (as all as associated compositions, systems, devices and instruments) that leverages the high-throughput genotyping capabilities of microarray-based analysis to generate data from a single set of interrogation sites (for example, a data from a single set of polymorphic loci in mixed DNA populations), which can then be used to both genotype and estimate copy number of a given locus or chromosome within the major and minor DNA populations within mixed nucleic acid populations.

Described herein are methods and systems for analyzing a mixed nucleic acid sample to detect differences in copy number of a target polynucleotide, such as a detection of copy number variants indicating chromosomal aneuploidy, as well as methods of genotyping such target polynucleotides even when present at low levels within a mixed nucleic acid population.

SUMMARY

This Summary is provided to introduce various aspects of the disclosure that are further described below in the Detailed Description. This Summary is not intended to limit the scope of the claimed subject matter. Other features, details, utilities, and advantages of the claimed subject matter will be apparent from the following written Detailed Description including those aspects illustrated in the accompanying drawings and defined in the appended claims.

In one aspect, the disclosure provides methods for analyzing a nucleic acid sample obtained from an organism. The nucleic acid sample can include DNA and/or RNA, or synthetic derivatives thereof. The nucleic acid sample can include cell-free DNA and/or cell-free RNA. In some embodiments, the nucleic acid sample includes a mixed nucleic acid population. The nucleic acid sample containing the mixed nucleic acid population can be obtained from a single organism. The mixed nucleic acid population can include nucleic acid of fetal origin and maternal origin. The mixed nucleic acid population can include nucleic acid originating from tumor and normal cells.

The methods described herein can further include obtaining or deriving from an organism a nucleic acid sample containing a mixed nucleic acid population. The obtaining or deriving optionally includes any one or more of the following steps: labeling (including bulk labeling or stochastic labeling), single-molecule labeling, amplification, ligation to other nucleic acid sequences, circularization, hybridization, target selection, methylation or binding to methylation-specific reagents, antibody binding, target capture, precipitation, elution, and the like, In some embodiments, the mixed nucleic acid sample includes a major subpopulation and a minor subpopulation. The major subpopulation is optionally present at greater than 50% of total nucleic acid in the mixed nucleic acid population. The major subpopulation can be present at greater than 50% of total nucleic acid in the nucleic acid sample. In some embodiments, the major and minor subpopulations each include a target sequence located in a first chromosomal region. The target sequence of the major and minor subpopulations can be the same sequence or overlapping sequences. In some embodiments, the target sequence contains a polymorphic site. The polymorphic site can include a sequence containing a first nucleotide variant and/or a second nucleotide variant, optionally at the same site. In some embodiments, the polymorphic sequence includes a single nucleotide polymorphism (SNP). The SNP can include a single nucleotide whose identity defines an allelic variant of the polymorphic site. The polymorphic site can include a major allele or a minor allele or both (e.g., in the case of a diploid organism).

In some embodiments, the methods described herein (as well as related compositions, kits, and systems) involve the selective enrichment of certain genetic sequences of interest. The selective enrichment can include targeted amplification, which may be performed in singleplex or multiplex formats. In some embodiments, the described methods can include use of target-specific primers or probes. Optionally, the methods include use of a molecular inversion probe. In some embodiments, the methods include hybridizing the primer or probe (e.g., the molecular inversion probe) to a target sequence. Optionally, the primer or probe can be extended in a target-specific manner. In some embodiments, the probe is a molecular inversion probe that hybridizes adjacent to or upstream of a polymorphic site. The methods can include extending the primer or probe by incorporating a nucleotide whose identity corresponds to the sequence of one or more polymorphisms in the polymorphic site.

In some embodiments, the methods described herein include genotyping the polymorphic site. In further embodiments, the genotyping includes hybridizing at least one nucleic acid fragment containing or derived from the nucleic acid population and containing the polymorphic site to an oligonucleotide probe. The oligonucleotide probe can optionally be located within an array of other probes, or can be hybridized to another oligonucleotide probe present in an array.

In some embodiments, the described methods further include detecting from the oligonucleotide array, using a detector, a first signal indicating the presence or absence of the first nucleotide variant ("A signal"). In some embodiments, the described methods include detecting a second signal indicating the presence or absence of the second nucleotide variant ("B signal"). In some embodiments, the described methods can include detecting both the first signal and the second signal from the same array. In some embodiments, the first signal can indicate the present or absence of a first allelic form of the polymorphic site ("A allele"). The second signal can indicate the present or absence of a second allelic form of the polymorphic site ("B allele"). In some embodiments, the major subpopulation includes the A allele and the minor subpopulation includes the B allele. In some embodiments, the described methods further include genotyping the major subpopulation, the minor subpopulation or both the major and minor subpopulation, optionally using the A signal, the B signal, or both the A and B signals. In some embodiments, the described methods further include estimating or calculating the copy number of the target nucleic acid sequence including the polymorphic site in the major subpopulation, the minor subpopulation or both the major and minor subpopulation, optionally using the A signal, the B signal or both the A and B signals. The methods can include calculating the copy number of the first chromosomal region using the A signal, the B signal or both the A and B signals. The methods can include detecting the presence or absence of an aneuploidy. In some embodiments, the methods can include calculating the relative proportions of nucleic acid derived from the major and minor subpopulations using the A signal, the B signal or both the A and B signals. The methods can include calculating the fetal fraction of the nucleic acid sample using the A signal, the B signal or both the A and B signals. In some embodiments, the methods can further include any one or more of the following steps: (a) determining the copy number of the first chromosomal region in the minor subpopulation using the first signal and the second signal; (b) determining the copy number of the first chromosomal region in the major subpopulation using the first signal and the second signal; (c) determining the genotype of the polymorphic site for the minor subpopulation using the first signal and the second signal; (d) determining the genotype of the polymorphic site for the major subpopulation using the first signal and the second signal, and (e) further including determining the relative amounts of the major subpopulation and the minor subpopulation in the mixed nucleic acid population using the first signal and the second signal.

In another aspect, the disclosure provides methods for determining a copy number variation in a mixed nucleic acid sample obtained from an organism, the method comprising one or more of the following steps:

a. isolating genomic DNA to form a mixed nucleic acid sample containing a mixed nucleic acid population that includes a major subpopulation and a minor subpopulation;

b. contacting the nucleic acid sample with a pool of linear molecular inversion probes to provide an annealing mixture comprising a plurality of linear molecular inversion probe-DNA fragment complexes;

c. dividing the annealing mixture into a first channel composition and a second channel composition;

d. adding a mixture of deoxynucleotides to each of the first and second channel composition, wherein the mixture of deoxynucleotides added to the first channel composition is different from the mixture of deoxynucleotides added to the second channel composition;

e. contacting the first and second channel compositions with a ligase to form first and second circularized probe compositions;

f. optionally contacting the first circularized probe composition and the second circularized probe composition with a first exonuclease to cleave remaining linear molecular inversion probes and nucleic acid fragments;

g. cleaving the first circularized and second probe compositions to form nucleic acid fragments containing or derived from the nucleic acid population;

h. amplifying the first and second nucleic acid fragments containing or derived from the nucleic acid population;

i. combining the first and second nucleic acid fragments containing or derived from the nucleic acid population;

j. digesting the first and second nucleic acid fragments containing or derived from the nucleic acid population;

k. hybridizing at least one nucleic acid fragment containing or derived from the nucleic acid population and containing the polymorphic site to an oligonucleotide probe of an oligonucleotide array;

l. labeling a surface-bound first and second nucleic acid fragments containing or derived from the nucleic acid population with a first agent that binds to the first nucleotide variant and a second agent that binds to the second nucleotide variant; and m. analyzing the intensity of a signal specific for the first agent and the intensity of a signal from the second agent to determine a copy number of a chromosome.

In another aspect, the disclosure provides a kit useful in the detection of fetal copy number variation comprising:

a. a capture device having a plurality of nucleic acid fragments corresponding at least one chromosomal target region attached thereto;

b. a plurality of molecular probes capable of hybridizing to a mixed nucleic acid population that includes a major subpopulation and a minor subpopulation, wherein the major and minor subpopulations each include a target sequence located in a first chromosomal region and containing a polymorphic site, wherein the polymorphic site can include combinations of a first nucleotide variant and a second nucleotide variant; and c. instructions for genotyping and detecting the polymorphic site.

These aspects and other embodiments of the disclosure can be further described by the following enumerated clauses:

1. A method for analyzing a mixed nucleic acid sample obtained from an organism, comprising:

obtaining or deriving from an organism a nucleic acid sample containing a mixed nucleic acid population that includes a major subpopulation and a minor subpopulation, wherein the major and minor subpopulations each include a target sequence located in a first chromosomal region and containing a polymorphic site, wherein the polymorphic site can include a first nucleotide variant, a second nucleotide variant or both the first and second nucleotide variants;

genotyping the polymorphic site, wherein the genotyping includes: (a) hybridizing at least one nucleic acid fragment containing or derived from the nucleic acid population and containing the polymorphic site to an oligonucleotide probe of an oligonucleotide array; and (b) detecting from the oligonucleotide array, using a detector, a first signal indicating the presence or absence of the first nucleotide variant ("A signal") and a second signal indicating the presence or absence of the second nucleotide variant ("B signal"). Optionally, the first nucleotide variant corresponds to a first allelic variant and the second nucleotide variant corresponds to a second allelic variant.

2. The method of clause 1, further including determining the copy number of the first chromosomal region in the minor subpopulation using the first signal and the second signal.

3. The method of clause 1, further including determining the copy number of the first chromosomal region in the major subpopulation using the first signal and the second signal.

4. The method of clause 1, further including determining the genotype of the polymorphic site for the minor subpopulation using the first signal and the second signal.

5. The method of clause 1, further including determining the genotype of the polymorphic site for the major subpopulation using the first signal and the second signal.

6. The method of clause 1, further including determining the relative amounts of the major subpopulation and the minor subpopulation in the mixed nucleic acid population using the first signal and the second signal.

7. The method of any of the preceding clauses, wherein the major subpopulation and the minor subpopulation originate from different sources in the organism.

8. The method of any of the preceding clauses, wherein the mixed nucleic acid population includes cell-free DNA.

9. The method of clause 8, wherein the cell-free DNA is obtained or derived from the organism's blood, plasma, serum, urine, stool or saliva.

10. The method of any of the preceding clauses, wherein the organism includes a tumor, the major subpopulation includes or is derived from normal tissue and the minor subpopulation includes or is derived from the tumor.

11. The method of any of the preceding clauses, wherein the organism is a pregnant female, the mixed nucleic acid population is cell-free DNA obtained from the pregnant female's blood, the major subpopulation includes or is derived maternal nucleic acid and the minor subpopulation includes or is derived from fetal nucleic acid.

12. The method of clause 11, wherein the minor subpopulation includes fetal DNA present at no greater than 20% of total DNA in the nucleic acid sample.

13. The method of clause 12, wherein the fetal DNA is no greater than 15% of total DNA in the nucleic acid sample.

14. The method of clause 12, wherein the fetal DNA is no greater than 10% of total DNA in the nucleic acid sample.

15. The method of clause 12, wherein the fetal DNA is no greater than 5% of total DNA in the nucleic acid sample.

16. The method of clause 1, wherein the fetal DNA is no greater than 15% and no less than 1% of total cell-free DNA in the nucleic acid sample.

17. The method of any of the preceding clauses, wherein the mixed nucleic acid population contains or is derived from cell-free DNA present in blood of the organism at concentration of no greater than 5 ng/mL and no less than 0.1 ng/mL.

18. The method of clause 1, wherein the amount of mixed nucleic acid population used is no greater than 50 ng, 40 ng, 30 ng, 15 ng, 10 ng, 5 ng, 3 ng or 1 ng.

19. The method of clause 1, wherein the polymorphic site includes a bi-allelic SNP, the first nucleotide variant is a first allelic variant of the SNP ("A allele") and the second nucleotide variant is a second allelic variant of the SNP ("B allele").

20. The method of any of the preceding clauses, wherein the detector includes a first detection channel and a second detection channel, and further including the steps of detecting the first signal in the first detection channel and the second signal in the second detection channel.

21. The method of clause 19, wherein the SNP can include the A allele or the B allele, and wherein the SNP genotype can be homozygous for the A allele ("AA"), homozygous for the B allele ("BB") or heterozygous ("AB").

22. The method of any one of the preceding clauses, wherein the step of genotyping further includes contacting the nucleic acid sample with a pool of linear molecular inversion probes to provide an annealing mixture.

23. The method of clause 22, wherein the pool of linear molecular inversion probes comprises at least 1,000 linear molecular inversion probes.

24. The method of clause 22, wherein the pool of linear molecular inversion probes comprises at least 5,000 linear molecular inversion probes.

25. The method of clause 22, wherein the pool of linear molecular inversion probes comprises at least 10,000 linear molecular inversion probes.

26. The method of clause 22, wherein the pool of linear molecular inversion probes comprises at least 20,000 linear molecular inversion probes.

27. The method of clause 22, wherein the pool of linear molecular inversion probes comprises less than 200,000 linear molecular inversion probes.

28. The method of clause 22, wherein the pool of linear molecular inversion probes comprises less than 100,000 linear molecular inversion probes.

29. The method of clause 22, wherein the pool of linear molecular inversion probes comprises less than 80,000 linear molecular inversion probes.

30. The method of any one of clauses 22-29, wherein at least 50% of the pool of linear molecular inversion probes binds DNA fragments from chromosomes 1, 5, 13, 18, 21, X, and Y.

31. The method of any one of clauses 22-29, wherein at least 60% of the pool of linear molecular inversion probes binds DNA fragments from chromosomes 1, 5, 13, 18, 21, X, and Y.

32. The method of any one of clauses 22-29, wherein at least 70% of the pool of linear molecular inversion probes binds DNA fragments from chromosomes 1, 5, 13, 18, 21, X, and Y.

33. The method of any one of clauses 22-29, wherein the ratio of the total number of linear molecular inversion probes to the total number of DNA fragment copies is about 40,000:1.

34. The method of any one of clauses 22-29, wherein the ratio of the total number of linear molecular inversion probes to the total number of DNA fragment copies is at least 15,000:1.

35. The method of any one of clauses 22-29, wherein the ratio of the total number of linear molecular inversion probes to the total number of DNA fragment copies is at least 30,000:1.

36. The method of any one of clauses 22-29, wherein the ratio of the total number of linear molecular inversion probes to the total number of DNA fragment copies is less than 100,000:1.

37. The method of any one of clauses 22-29, wherein the ratio of the total number of linear molecular inversion probes to the total number of DNA fragment copies is less than 60,000:1.

38. The method of any one of the preceding clauses, wherein the step of genotyping further includes dividing the annealing mixture into a first channel composition and a second channel composition.

39. The method of clause 38, wherein the first channel composition comprises a mixture of dATP and dTTP.

40. The method of clause 38 or 39, wherein the first channel composition is substantially free of dGTP or dCTP.

41. The method of any one of clauses 38-40, wherein the second channel composition comprises a mixture of dGTP and dCTP.

42. The method of any one of clauses 38-41, wherein the second channel composition is substantially free of dATP or dTTP.

43. The method of any one of the preceding clauses, wherein the step of genotyping further includes adding a mixture of deoxynucleotides to each of the first and second channel composition, wherein the mixture of deoxynucleotides added to the first channel composition is different from the mixture of deoxynucleotides added to the second channel composition.

44. The method of any one of the preceding clauses, wherein the step of genotyping further includes contacting the first and second channel compositions with a ligase to form first and second circularized probe compositions.

45. The method of any one of the preceding clauses, wherein the step of genotyping further includes cleaving the first circularized and second probe compositions to form nucleic acid fragments containing or derived from the nucleic acid population.

46. The method of any one of the preceding clauses, wherein the step of genotyping further includes amplifying the first and second nucleic acid fragments containing or derived from the nucleic acid population.

47. The method of any one of the preceding clauses, wherein the step of amplifying in carried out in the presence of a polymerase.

48. The method of clause 47, wherein the polymerase is a hot-start polymerase comprising the polymerase and a polymerase inhibitor.

49. The method of clause 48, wherein the polymerase inhibitor is disassociated from the polymerase when the temperature is at least 40° C.

50. The method of any one of the preceding clauses, wherein the step of genotyping further includes combining the first and second nucleic acid fragments containing or derived from the nucleic acid population.

51. The method of any one of the preceding clauses, wherein the step of detecting further includes labeling a surface-bound first and second nucleic acid fragment containing or derived from the nucleic acid population with a first agent that binds to the first allelic variant and a second agent that binds to the second allelic variant.

52. The method of clause 51, wherein the first agent has an antibody.

53. The method of clause 51 or 52, wherein the first agent has a complementary sequence to a portion of the first target sequence.

54. The method of any one of clauses 51-53, wherein the first agent further comprises a recognition element conjugated to the complementary sequence.

55. The method of clause 54, wherein the recognition element is biotin.

56. The method of any one of clauses 51-55, wherein the first agent further comprises a fluorescently labeled avidin.

57. The method of any one of clauses 51-56, wherein the first agent further comprises an antibody that binds avidin.

58. The method of clause 57, wherein the antibody that binds avidin is labeled with a biotin.

59. The method of any one of clauses 51-58, wherein the first agent further comprises an antibody that binds the recognition element.

60. The method of clause 59, wherein the antibody that binds the recognition element is labeled with a reporter.

61. The method of any one of clauses 51-60, wherein the first agent comprises a fluorophore.

62. The method of clause 61, wherein the fluorophore of the first agent has a fluorescence emission peak between about 640 nm and about 680 nm.

63. The method of clause 61 or 62, wherein the fluorophore of the first agent is allophycocyanin.

64. The method of clause 51, wherein the second agent has a complementary sequence to a portion of the second target sequence.

65. The method of clause 64, wherein the second agent further has a recognition element conjugated to the complementary sequence.

66. The method of clause 65, wherein the recognition element is FAM.

67. The method of any one of clauses 64-66 wherein the second agent further comprises a first antibody that binds the recognition element.

68. The method of any one of clauses 64-66, wherein the second agent further comprises a second antibody that binds the first antibody.

69. The method of clause 68, wherein the first antibody, the second antibody, or both the first and second antibody are labeled with a fluorophore.

70. The method of clause 69, wherein the fluorophore of the second agent has a fluorescence emission peak between about 560 nm and about 600 nm.

71. The method of clause 70, wherein the fluorophore of the second agent is phycoerythrin.

72. The method of any one of the preceding clauses, wherein the step of contacting the cell-free DNA composition occurs in reaction volume that is less than 50 µL.

73. The method of any one of the preceding clauses, wherein the step of contacting the cell-free DNA composition occurs in reaction volume that is less than 40 µL.

74. The method of any one of the preceding clauses, wherein the step of contacting the cell-free DNA composition occurs in reaction volume that is less than 30 µL.

75. The method of any one of the preceding clauses, wherein the step of contacting the cell-free DNA composition occurs in reaction volume that is less than 20 µL.

76. The method of any one of the preceding clauses, wherein the fetal DNA is about 30% of total DNA in the nucleic acid sample.

77. The method of any one of the preceding clauses, wherein the fetal DNA is no greater than 30% of total DNA in the nucleic acid sample.

78. The method of any one of the preceding clauses, wherein the fetal DNA is more than 30% of total DNA in the nucleic acid sample.

79. A kit useful in the detection of fetal copy number variation comprising:
a. a capture device having a plurality of nucleic acid fragments corresponding at least one chromosomal target region attached thereto; b. a plurality of molecular probes capable of hybridizing to a mixed nucleic acid population that includes a major subpopulation and a minor subpopulation, wherein the major and minor subpopulations each include a target sequence located in a first chromosomal region and containing a polymorphic site, wherein the polymorphic site can include combinations of a first nucleotide variant and a second nucleotide variant; and c. instructions for genotyping and detecting the polymorphic site.

80. The kit of clause 77, wherein the capture device is a microarray.

81. The kit of clause 77 or 78, wherein the chromosomal target region is on one or more of chromosomes 1, 5, 13, 18, 21, X, and Y.

82. The kit of any one of clauses 77 to 79, wherein molecular probes are designed to genotype a single nucleotide polymorphism on one or more of chromosomes 1, 5, 13, 18, 21, X, and Y.

83. A method for detecting a copy number in a fetus, comprising: obtaining a biological sample from a subject who is a pregnant female, the biological sample including nucleic acid of both maternal and fetal origin containing a target nucleic acid sequence located on a first chromosome, the target nucleic acid sequence containing a polymorphic site for a single nucleotide polymorphism (SNP); generating a population of nucleic acid fragments containing or derived from the target nucleic acid sequence; conducting a first assay comprising (a) contacting the population of nucleic acid fragments with an oligonucleotide array containing a first oligonucleotide probe configured to hybridize to the target nucleic acid sequence containing the polymorphic site of the SNP; and (b) detecting, using a detector, first signals indicating hybridization of the oligonucleotide probe to one or more nucleic acid fragments of the population containing a first allelic variant ("A allele") of the SNP and second signals indicating hybridization of the oligonucleotide probe to one or more nucleic acid fragments of the population containing a second allelic variant ("B allele") of the SNP; and determining, using the first signals and the second signals, any one or more of the following: (i) the copy number of the first chromosome in the fetus; (ii) a fetal genotype for the SNP; (iii) a maternal genotype for the SNP; and (iv) a fetal fraction of the sample.

84. The method of clause 83, further comprising calculating the observed B-allele frequency (BAF) for the allelic variants of the SNP present in the sample.

85. The method of clause 84, further including calculating the fetal fraction of the sample using the BAF.

86. The method of clause 84, wherein the polymorphic site of the SNP can be homozygous for the A allele ("AA"), homozygous for the B allele ("BB") or heterozygous ("AB").

87. The method of any of clauses 83-86, wherein the detector has a first and a second detection channel, and the genotyping further includes detecting the first signals in the first channel and the second signals in the second channel.

88. The method of clause 87, wherein the first signals in the first channel indicate the amount of A allele present in the nucleic acid population and the second signals indicate the amount of B allele present at nucleic acid population.

89. The method of clause 88, wherein determining the copy number of the first chromosome in the fetus includes determining a ratio of a first value to a second value.

90. The method of clause 86, further including determining a first maternal SNP genotype.

91. The method of clause 83, wherein the nucleic acid sample includes maternal blood, plasma or serum and the nucleic acid of both maternal and fetal origin includes cell-free DNA (cfDNA).

92. The method of clause 83, wherein the fetal DNA is no greater than 20% of total DNA in the nucleic acid sample.

93. The method of clause 83, wherein the fetal DNA is no greater than 15% of total DNA in the nucleic acid sample.

94. The method of clause 83, wherein the fetal DNA is no greater than 10% of total DNA in the nucleic acid sample.

95. The method of clause 83, wherein the fetal DNA is no greater than 5% of total DNA in the nucleic acid sample.

96. The method of clause 83, wherein the fetal DNA is about 30% of total DNA in the nucleic acid sample.

97. The method of clause 83, wherein the fetal DNA is no greater than 30% of total DNA in the nucleic acid sample.

98. The method of clause 83, wherein the fetal DNA is more than 30% of total DNA in the nucleic acid sample.

BRIEF DESCRIPTIONS OF THE DRAWINGS

DETAILED DESCRIPTION

Figure 1:
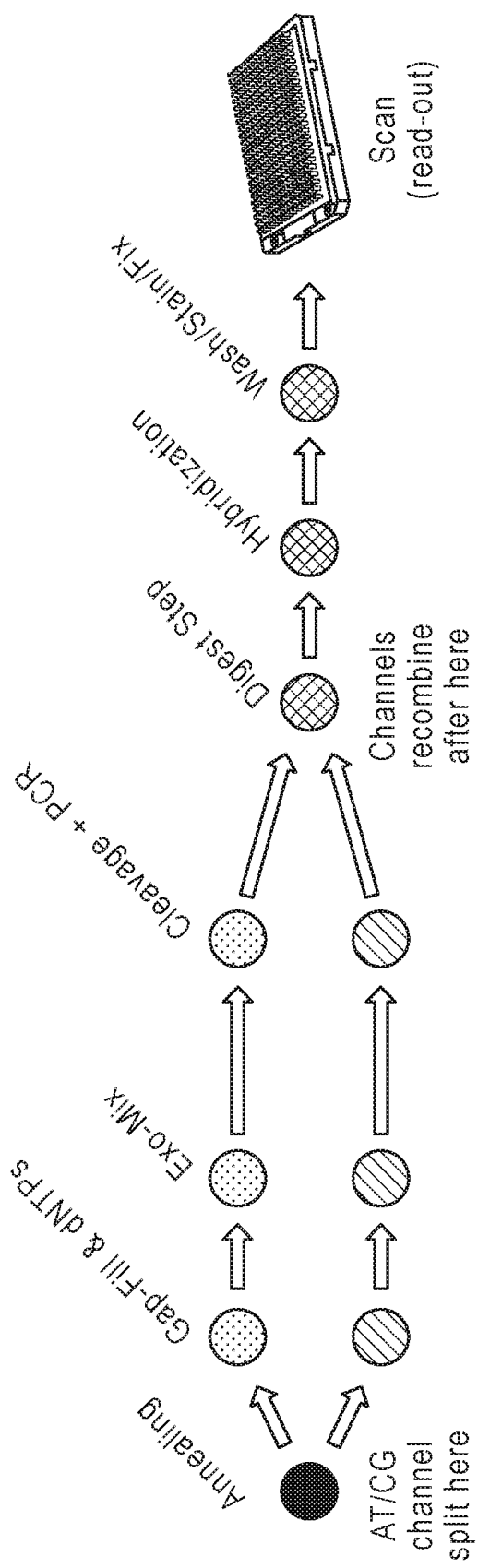
FIG. 1 is a diagrammatic view of a method for analyzing a mixed nucleic acid sample in accordance with the present disclosure, showing that the mixed nucleic acid sample is split into an A/T channel and a C/G channel and then recombined several steps later for hybridization and staining steps.

The present disclosure has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

Throughout this disclosure, various aspects of this disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present disclosure may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. *I-IV*), *Using Antibodies: A Laboratory Manual, Cells: A Laboratory Manual, PCR Primer: A Laboratory Manual*, and Molecular *Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Definitions

As used in this application, the singular form "a," "an," and "the" include plural references unless the context clearly dictates otherwise. For example, the term "an agent" includes a plurality of agents, including mixtures thereof.

All references cited herein are incorporated herein in their entireties for all their purposes. To the extent any reference includes a definition or uses a claim term in a manner inconsistent with the definitions and disclosure set forth herein, the definitions and disclosure of this application will control.

As used herein, "allele" refers to one specific form of a nucleic acid sequence (such as a gene) within a cell, an individual or within a population, the specific form differing from other forms of the same gene in the nucleic acid sequence of at least one, and frequently more than one, variant sites within the sequence of the gene. The sequences at these variant sites that differ between different alleles are termed "variances", "polymorphisms", or "mutations". The variants in the sequence can occur as a result of SNPs, combinations of SNPs, haplotype methylation patterns, insertions, deletions, and the like. An allele may comprise the variant form of a single nucleotide, a variant form of a contiguous sequence of nucleotides from a region of interest on a chromosome, or a variant form of multiple single nucleotides (not necessarily all contiguous) from a chromosomal region of interest. At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

As used herein, "an array" or "a microarray" comprises a support, preferably solid, with nucleic acid probes attached to the support. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., *Science,* 251: 767-777 (1991). Each of which is incorporated by reference in its entirety for all purposes. The probes can be of any size or sequence, and can include synthetic nucleic acids, as well as analogs or derivatives or modifications thereof, as long as the resulting array is capable of hybridizing under any suitable conditions with a nucleic acid sample with sufficient specificity as to discriminate between different target nucleic acid sequences of the sample. In some embodiments, the probes of the array are at least 5, 10 or 20 nucleotides long. In some embodiments, the probes are no longer than 25, 30, 50, 75, 100, 150, 200 or 500 nucleotides long. For example, the probes can be between 10 and 100 nucleotides in length.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on three-dimensional matrices, beads, gels, polymeric surfaces, fibers such as optical fibers, glass or any other appropriate substrate. (See U.S. Pat. Nos. 5,770,358, 5,789,162, 5,708,153, 6,040,193 and 5,800,992, which are hereby incorporated by reference in their entirety for all purposes.)

In some embodiments, arrays useful in connection with the methods and systems described herein include commercially available from Thermo Fisher Scientific (formerly Affymetrix) under the brand name GeneChip® and are directed to a variety of purposes, including genotyping and gene expression monitoring for a variety of eukaryotic and prokaryotic species. Methods for preparing a sample for hybridization to an array and conditions for hybridization are disclosed in the manuals provided with the arrays, for example, those provided by the manufacturer in connection with products, such as the OncoScan® FFPE Assay Kit, and related products.

As used herein, "cell-free nucleic acid" means nucleic acid molecules of present in the body of an organism but that are not contained within any intact cells. The cell-free nucleic acid can include DNA ("cell-free DNA") or RNA ("cell-free RNA") or derivatives or analogs thereof. The cell-free nucleic acid can be obtained from blood, plasma, saliva, or urine. The cell-free DNA or RNA can include circulating cell-free DNA or RNA, i.e., cell-free DNA or RNA found in the plasma fraction of blood.

It will be appreciated that numerous methods and kits are known to one of skill in the art for the purpose of obtaining cell-free DNA from a sample, such as human blood plasma, serum, urine, stool or saliva.

As used herein, "genome" designates or denotes the complete, single-copy set of genetic instructions for an organism as coded into the DNA of the organism. A genome may be multi-chromosomal such that the DNA is cellularly distributed among a plurality of individual chromosomes. For example, in humans there are 22 pairs of chromosomes plus a gender associated XX or XY pair.

As used herein, "genotyping" refers to the determination of the nucleic acid sequence information from a nucleic acid sample at one or more nucleotide positions. The nucleic acid sample may contain or be derived from any suitable source, including the genome or the transcriptome. In some embodiments, genotyping may comprise the determination of which allele or alleles an individual carries at one or more polymorphic sites. For example, genotyping may include or the determination of which allele or alleles an individual carries for one or more SNPs within a set of polymorphic sites. For example, a particular nucleotide in a genome may be an A in some individuals and a C in other individuals. Those individuals who have an A at the position have the A allele and those who have a C have the B allele. In a diploid organism the individual will have two copies of the sequence containing the polymorphic position so the individual may have an A allele and a B allele or alternatively two copies of the A allele or two copies of the B allele. Those individuals who have two copies of the B allele are homozygous for the B allele, those individuals who have two copies of the A allele are homozygous for the B allele, and those individuals who have one copy of each allele are heterozygous. The array may be designed to distinguish between each of these three possible outcomes. A polymorphic location may have two or more possible alleles and the array may be designed to distinguish between all possible combinations. In some embodiments, one or more polynucleotides (or a portion or portions of the polynucleotide, its amplification products, or complements thereof) that contain a sequence of interest (e.g., one or more SNP or mutation) can be processed by other techniques such as sequencing. Therefore, in some embodiments, the polynucleotides can be sequenced for genotyping or determining the presence or absence of the polymorphism or mutation. The sequencing can be done via various methods available in the art, e.g., Sanger sequencing method that can be performed by, e.g., SeqStudio® Genetic Analyzer from Applied Biosystems) or Next Generation Sequencing (NGS) method, e.g., Ion Torrent NGS from Thermo Fisher or Illumina NGS. In some embodiments, genotyping includes detecting a single nucleotide mutation that arises spontaneously in the genome, amongst a background of wild-type nucleic acid. In some embodiments, genotyping includes determining fetal blood type from a sample of maternal blood.

The term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multi-chromosomal genome and from one genome to another. In the case of the human genome, the entire DNA mass of a given chromosome is usually greater than 100,000,000 bp. For example, the size of the entire human genome is about $3 \times 10^9$ bp. The largest chromosome, chromosome no. 1, contains about $2.4 \times 10^8$ bp while the smallest chromosome, chromosome no. 22, contains about $5.3 \times 10^7$ bp. In some embodiments, chromosomes of interest in connection with the methods and systems of the present disclosure include those chromosomes that are associated with a chromosomal abnormality, such as chromosomes 13, 18, 21, X, and Y. It will be further appreciated that other chromosomes not associated with a particular chromosomal abnormality, such as aneuploidy, can be of interest in connection with the methods and systems of the present disclosure as reference chromosomes. It will be appreciated that a reference chromosome can be any of the chromosomes in a genome that are not associated with a particular chromosomal abnormality, such as aneuploidy, such as chromosomes 1 and 5.

As used herein, "chromosomal region" means a portion of a chromosome. The actual physical size or extent of any individual chromosomal region can vary greatly. The term "region" is not necessarily definitive of a particular one or more genes because a region need not take into specific account the particular coding segments (exons) of an individual gene. In some embodiments, a chromosomal region will contain at least one polymorphic site.

As used herein, "chromosomal abnormalities" or "chromosomal abnormality" can include any genetic abnormality including but not limited to aneuploidy, such as trisomy 21 (a.k.a. Down syndrome); trisomy 18 (a.k.a. Edwards syndrome); trisomy 13 (a.k.a. Patau syndrome); XXY (a.k.a. Klinefelter's syndrome); monosomy 18; X (a.k.a. Turner syndrome); XYY (a.k.a. Jacobs Syndrome), or XXX (a.k.a. Trisomy X); trisomy associated with an increased chance of miscarriage (e.g., Trisomy 15, 16, or 22); and the like, as well as other genetic variations, such as mutations, insertions, additions, deletions, translocation, point mutation, trinucleotide repeat disorders and/or SNPs. While the present disclosure describes certain examples and embodiments related to the detection of chromosomal abnormalities in a fetus, it will be appreciated that the methods and system described herein can be used to detect chromosomal abnormalities in other disease states, such as cancer.

As used herein, "maternal sample" can be any sample taken from a pregnant mammal which comprises both fetal and maternal cell-free DNA. Preferably, maternal samples for use in connection with the present disclosure are obtained through relatively non-invasive means, e.g., phlebotomy, saliva or urine collection, or other standard techniques for extracting peripheral samples from a subject.

As used herein "nucleotide" refers to a base-sugar-phosphate combination. Nucleotides are monomeric units of a nucleic acid sequence (DNA and RNA). The term nucleotide includes ribonucleoside triphosphates ATP, UTP, CTG, GTP and deoxyribonucleoside triphosphates (dNTPs) such as dATP, dCTP, dITP, dUTP, dGTP, dTTP, or derivatives thereof. Such derivatives include, for example, [αS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP.

As used herein, "polymorphism" refers to the occurrence of two or more genetically determined alternative sequences in a population. The alternative sequences can include alleles (e.g., naturally occurring variants) or spontaneously arising mutations that only occur in one or few individual organisms. A "polymorphic site" can refer to the nucleic acid position(s) at which a difference in nucleic acid sequence occurs. A polymorphism may comprise one or more base changes, an insertion, a repeat, or a deletion. A polymorphic locus may be as small as one base pair. Polymorphic sites include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements. The first identified variant or allelic form is arbitrarily designated as the reference form and other variant or allelic forms are designated as alternative or variant or mutant alleles. The variant or allelic form occurring most frequently in a selected nucleic acid population is sometimes referred to as the wildtype form. In some embodiments, the wildtype form can be referred to as a "major subpopulation" and the mutant can be referred to as ta "minor subpopulation". In some embodiments, the more frequently occurring allele can be referred to as a "major subpopulation" and the rarer or less frequently occurring allele can be referred to as ta "minor subpopulation". Diploid organisms may be homozygous or heterozygous for allelic forms. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens. SNPs are positions at which two alternative bases occur at appreciable frequency (>1%) in the human population, and are the most common type of human genetic variation.

As used herein, "sample obtained from an organism" includes but is not limited to any number of tissues or fluids, such as blood, urine, serum, plasma, lymph, saliva, stool, and vaginal secretions, of virtually any organism. In some embodiments, a sample obtained from an organism can be a mammalian sample. And in some embodiments, a sample obtained from an organism can be a human sample. In some embodiments, a sample obtained from an organism can be a maternal sample.

Genotyping

In some embodiments, the methods described in the present disclosure include a step of genotyping. The genotyping can include determining the sequence of at least one nucleotide within a target nucleic acid sequence. In some embodiments, the step of genotyping involves analyzing a mixed nucleic acid population that includes a major subpopulation and a minor subpopulation, wherein the major and minor subpopulations each include a target sequence located in a first chromosomal region and containing a polymorphic site. In some embodiments, the methods described herein are used to genotype the major subpopulation. In some embodiments, the methods described herein are used to genotype the minor subpopulation. In some embodiments, the methods described herein are used to genotype both the major subpopulation and the minor subpopulation.

It will be appreciated that genotyping can be carried out in any manner useful for the identification of polymorphic sites in a target sequence of a nucleic acid sample. In some embodiments, methods of genotyping useful in connection with the present disclosure include those methods useful for SNP detection. Platforms for SNP detection are well known in the art. Suitable methods for genotyping include variations of single nucleotide extension, use of allele-specific probes, ligation-based allelic discrimination, and the like.

In the context of array based assays, a variety of genotyping methods are available. In some embodiments, the array surface is divided into features, each feature containing multiple sites that include copies of substantially identical oligonucleotides configured to bind to a particular target nucleic acid sequence. Hybridization of nucleic acid molecules to different locations on the array can be detected and quantified. One suitable method is to use any array containing allele-specific probes that selectively bind only to certain alleles and not others. In other embodiments, the array contains probes that bind non-selectively to all of the different forms of an allele, but then is extended or otherwise modified in an allele-specific manner to generate an allele-specific product. For example, the probe of the array can be elongated via template-dependent nucleotide polymerization. Alternatively, the probe can be elongated via sequence-dependent ligation of a tag oligonucleotide, which may contain a signal-generating moiety. In still, allele-specific products (e.g., allele-specific nucleotide extension products or ligation products) can be generated off-array, and then hybridized to an array containing probes that discriminate between the various extension products. Signals emitted from the array indicating hybridization of nucleic acid molecules to specific array probes can be detected and quantified. Examples of genotyping array products include the Affymetrix Axiom® arrays and the Affymetrix OncoScan arrays (Thermo Fisher Scientific) as well as Illumina's BeadChip® and Infinium® arrays, Suitable array-based genotyping methods are described, for example, in Hoffman et al, Genomics 98(2):79-89 (2011) and Shen et al., Mutation Research 573:70-82 (2005), both of which are incorporated herein in their entireties.

One method useful for genotyping variations in nucleic acid sequence (including through use of microarrays) is the molecular inversion probe (MIP) assay. See for example, U.S. Pat. No. 6,858,412, incorporated herein by reference in its entirety pertaining to the implementation of the MIP assay generally.

Figure 2:
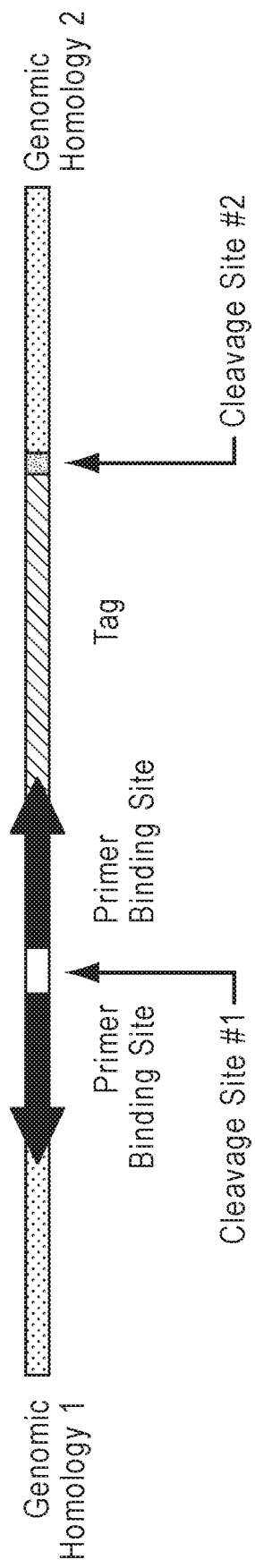
FIG. 2 is a diagrammatic view of a molecular inversion probe (MIP) used in a method in accordance with the present disclosure.

In general MIP probes include at least a 5'-target sequence, a 3'-target sequence, a 5'-primer site and/or a 3'-primer site, a tag sequence, and one or more cleavage sites. In one exemplary embodiment, MIP probes useful in connection with the present disclosure can be represented as shown in FIG. 2. The MIP probe of FIG. 2 includes genomic homology 1 and genomic homology 2 that correspond to target a sequence on a chromosomal region that is a known SNP locus. Genomic homology 1 and genomic homology 2 are designed to have a one nucleotide gap in the probe after the probe has been hybridized to a nucleic acid fragment (e.g. a cell-free DNA fragment). In addition to genomic homology 1 and genomic homology 2 the MIP probes useful in connection with some embodiments of the disclosure include a first primer binding site and a second primer binding site, a tag sequence and two cleavage sites.

It will be appreciated that pools of MIP probes can be applied to the methods and systems described herein for multiplex detection of SNPs in the mixed nucleic acid sample. For example, in some embodiments, a pool of MIP probes can be pulled from the commercially available MIP probes sets used in connection with the OncoScan® product available from Thermo Fisher Scientific. For example, in some embodiments, a pool of about 48,000 MIP probes corresponding to SNP loci in chromosomes 13, 18, 21, X, and Y can be pulled from the OncoScan® product. In addition, it will be appreciated that additional pools of MIP probes, such as those corresponding to SNP loci on chromosomes 1 and 5 can be pulled from the OncoScan® product for use as reference probes. In some embodiments, at least 50%, at least 60%, or at least 70% of the MIPS in the pool of MIP probes bind to DNA fragments from chromosomes 1, 5, 13, 18, 21, X, and Y.

In some embodiments, the pool of MIP probes comprises at least 1,000 MIPS, at least 5,000, at least 10,000, or at least 20,000 MIPS. In some embodiments, the pool of MIP probes comprises less than 200,000, less than 100,000, or less than 80,000 MIPS.

Figure 3:
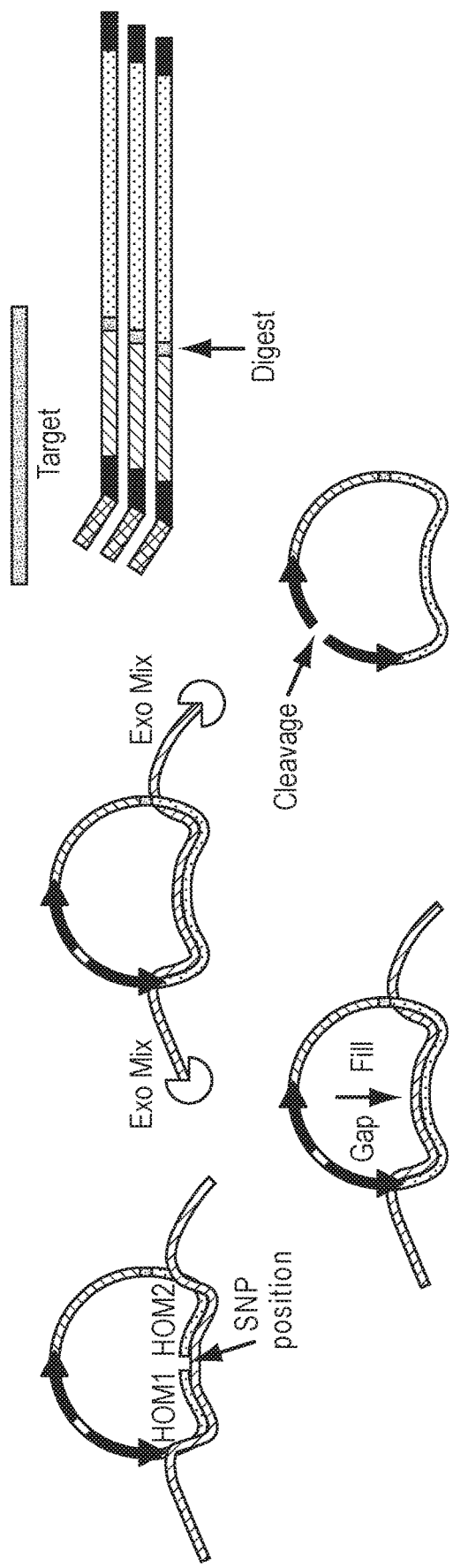
FIG. 3 is diagrammatic views of a MIP process showing from left to right a MIP binding to a nucleic acid over a SNP position, the SNP position being gap-filled and ligated to form a circularized MIP, treating the nucleic acid sample with an exonuclease, cleaving the circularized MIP, amplifying a portion of the cleaved MIP, and digesting the amplified product.

An exemplary MIP assay process useful in connection with the present disclosure is shown in FIG. 3. Briefly, the MIP probe can be hybridized to a target sequence located in a first chromosomal region containing a polymorphic site in an annealing step. The annealing step can be carried out according to any method commonly known in the art, especially according to manufacturer instructions for a commercially available MIP probe set. The step of annealing provides a plurality of linear molecular inversion probe-DNA fragment complexes, such that the genomic homology 1 and genomic homology 2 sequences hybridize to the chromosomal region containing a polymorphic site with a one nucleotide gap between the ends of the hybridized probe.

In some embodiments, the total amount of DNA fragments or mixed nucleic acid population is less than 50 ng, less than 40 ng, less than 30 ng, less than 20 ng, less than 15 ng, or less than 10 ng. In some embodiments, the ratio of the total number of MIPS to the total number of DNA fragment copies is at least about 15,000:1 or at least about 30,000:1. In some embodiments, the ratio of the total number of MIPS to the total number of DNA fragment copies is less than 100,000:1 or less than 60,000:1. In some embodiments, the ratio of the total number of MIPS to the total number of DNA fragment copies is about 40,000:1.

In some embodiments, the annealing step is performed in a reaction volume that is less than 50 µL, less than 40 µL, less than 30 µL, less than 20 µL, or less than 15 µL. In some embodiments, the reaction volume is at least 5 µL or at least 10 µL.

In some embodiments, the mixed nucleic acid population contains or is derived from cell-free DNA present in blood, srum and/or plasma of the organism at a concentration of no greater than 5 ng/mL and no less than 0.1 ng/mL. In some embodiments, the mixed nucleic acid population contains or is derived from cell-free DNA present in blood, srum and/or plasma of the organism at concentration of less than 5 ng/mL, less than 4 ng/mL, less than 3 ng/mL, less than 2 ng/mL, less than 1 ng/mL, less than 0.5 ng/mL, or less than 0.3 ng/mL. In some embodiments, the mixed nucleic acid population contains or is derived from cell-free DNA present in blood, srum and/or plasma of the organism at concentration of greater than 0.1 ng/mL, greater than 0.2 ng/mL, greater than 0.3 ng/mL, greater than 0.5 ng/mL, greater than 1 ng/mL, greater than 2 ng/mL, or greater than 3 ng/mL.

After the annealing step is completed, the annealing mixture may or may not be separated into a first channel and a second channel, depending on the particular genotyping application. In some embodiments, the annealing mixture can be separated into a first channel and a second channel (as shown in FIG. 1). In such an embodiment, the annealing mixture is split into a first channel composition and a second channel composition that can be carried forward through genotyping process. In some embodiments, the annealing mixture is not split into a first channel and a second channel, but rather carried on as a single reaction.

In some embodiments, the annealing mixture can be subjected to a ligation step, also referred to as a "gap-fill" step to incorporate nucleotides in the gap between genomic homology 1 and genomic homology 2 of the linear MIP, as shown in FIG. 3. For the gap fill reaction, any known method in the art will suffice. For example, a mix of deoxynucleotides (dATP, dCTP, dGTP, dTTP, dUTP) can be added to a reaction mix, as well as a polymerase, ligase and other reaction components and incubating at about 60° C. for about 10 minutes, followed by incubation at 37° C. for about 1 minute. Following annealing and ligation, the MIP may become circularized. In some embodiments, the nucleotides added to the first and second channel may be the same or different.

In some embodiments, where it is advantageous to add different sets of deoxynucleotides to the gap-fill reaction, the deoxynucleotides added to one of the channels can be dATP and dTTP, while the deoxynucleotides added to one of the other channels can be dCTP and dGTP. It will be appreciated that the different deoxynucleotide mixtures can be added to either channel. In this way, each channel can selectively detect different SNP alleles in a first circularized probe composition and a second circularized probe composition. In some embodiments, a channel may be substantially free of dGTP, dCTP, or a mixture thereof. In some embodiments, a channel may be substantially free of dATP, dTTP, or a mixture thereof.

It will be appreciated that the ligase used in the gap-fill step is not particularly preferred, and can be any ligase known in the art, and according to any standard protocol known in the art. Many ligases are known and are suitable for use in the connection with the present disclosure for the gap-fill reaction. See for example, Lehman, Science, 186: 790-797 (1974); Engler et al, DNA Ligases, pages 3-30 in Boyer, editor, The Enzymes, Vol. 15B (Academic Press, New York, 1982); and the like. Optional ligases for use in connection with the MIP gap-fill reaction include, but are not limited to, T4 DNA ligase, T7 DNA ligase, E. coli DNA ligase, Taq ligase, Pfu ligase, and Tth ligase. Protocols for use of such ligases are well known (See for example, Barany, PCR Methods and Applications, 1: 5-16 (1991); Marsh et al, Strategies, 5: 73-76 (1992); and the like). In some embodiment, the ligase can be a thermostable or (thermophilic) ligase, such as pfu ligase, Tth ligase, Taq ligase and Ampligase™ DNA ligase (Epicentre Technologies, Madison, Wis.).

In some embodiments, the respective circularized probe compositions, when there are more than one, can be subjected to an exonuclease digestion step, as shown in FIG. 3. The purpose of the exonuclease digestion step is to digest/remove any remaining nucleic acid fragments from the nucleic acid sample obtained from an organism, and to digest/remove any remaining uncircularized MIPs. It will be appreciated that such an optional digestion step can improve later PCR amplification by removing nucleic acid fragments that may interfere with the PCR reaction, or may form chimeric products that interfere with further processing of the sample later in the process. Suitable 3'-exonucleases include, but are not limited to, exo I, exo III, exo VII, exo V, and polymerases, as many polymerases have excellent exonuclease activity, etc.

After optional removal of uncircularized MIPS and DNA fragments, the circularized probes, in some embodiments, first circularized probes and second circularized probes can be cleaved to form to form a first linearized probe composition and a second linearized probe composition. It will be appreciated that the cleaving can be accomplished according to any method known in the art suitable for use in connection with the present teachings. In some embodiments, one or more circulized probes, e.g., the first and/or second circulizaed probes are single-stranded. In some embodiments, the circulaized probe(s) is/are double-stranded. In some embodiments, the circulaized probes are cleaved to form linearized probes. In some embodiments, there are one or more enzymes to be used to linearize the probes. In some embodiments, an enzyme that is capable of cleaving a single-stranded nucleic acid can be used to linearize the probes. In some embodiments, such an enzyme cleaving a single-stranded nucleic acid is uracil-N-glycosylase. In some other embodiments, one or more restriction enzymes can be used to linearize the probes. In some embodiments, the step of cleaving can be catalyzed by adding an ezyme such as uracil-N-glycosylase or a restriction enzyme to the linearized probe composition, and in some embodiments, the first and second linearized probe composition, cleaving the circular probes to form a first linearized probe composition and a second linearized probe composition. Suitable restriction enzymes include, but are not limited to AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BacI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BscRI, BscYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EacI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinPlI, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MsII, MspA1I, MspI, MwoI, NaeI, NarI, Nb.BbvCI, Nb.BsmI, Nb.BsrDI, Nb.BtsI, NciI, Ncof, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, Tagαl, TfiI, TliI, TseI, Tsp45I, Tsp509I, TspMI, TspRI, Tth111I, XbaI, XcmI, XhoI, XmaI, XmnI, and ZraI. It will be appreciated that the MIP probe can be designed to contain one or more, and in some embodiments two, restriction sites. In the case where MIPs are designed with two restriction sites, one of skill in the art will understand how to design the MIPs such that the restriction enzymes will act selectively on each cleavage site of the MIP.

As mentioned above, the MIP probe can be designed with one or two primer sites. As used herein, a "universal priming site" is a site to which a universal primer will hybridize. In general, "universal" refers to the use of a single primer or set of primers for a plurality of amplification reactions. For example, in the detection or genotyping of a 100 different target sequences, all the MIPs may share the identical universal priming sequences, allowing for the multiplex amplification of the 100 different probes using a single set of primers. This allows for ease of synthesis (e.g. only one set of primers is made), resulting in reduced costs, as well as advantages in the kinetics of hybridization. Most importantly, the use of such primers greatly simplifies multiplexing in that only two primers are needed to amplify a plurality of probes. In general, the universal priming sequences/primers each range from about 12 to about 40 base pairs in length. Suitable universal priming sequences are known to one of skill in the art, and specifically include those exemplified herein. In some embodiments, the MIP is also designed with a tag sequence, or a barcode sequence, that will allow for specific detection of two channel probes using a two-color system. In such an example, the universal primer sequence at one end of the linearized probes, either the 5'- or 3'-end, depending on the application and the detection platform, will contain a specific sequence to recognize a particular colored label. Thus it can be advantageous to design a MIP to have a restriction site between two universal 3'- and 5'-ends of universal primers.

Once the circularized probes are cleaved to form linearized probes, the probes can be subjected to an amplifying step of the first linearized probe composition in the presence of a first tailed primer to form a first amplified product composition, and amplifying the second linearized probe composition in the presence of a second tailed primer to form a second amplified product composition, wherein the first tailed primer has a tail sequence that is different from the second tailed primer. The amplification step can be carried out by any method known in the art. The PCR reaction can be carried out in the presence of a polymerase useful in connection with the present disclosure, such as USD Taq. In some embodiments, the amplification step is carried out in the presence of a hot-start polymerase comprising the polymerase and a polymerase inhibitor. In some embodiments, the polymerase inhibitor is disassociated from the polymerase when the temperature is at least 40° C. In some embodiments, the amplification step is carried out in the presence of Titanium Taq polymerase. In some embodiments, the amplification step is carried out in the presence of Platinum SuperFi DNA Polymerase.

The present disclosure also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 and U.S. patent application Ser. No. 09/513,300, which are incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA,* 87, 1874 (1990) and WO90/06995), selective amplification of target polynucleic acid sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NASBA). (See, U.S. Pat. Nos. 5,409,818, 5,554,517, and 6,063,603, each of which is incorporated herein by reference). Other amplification methods that may be used include: Qbeta Replicase, described in PCT Patent Application No. PCT/US87/00880, isothermal amplification methods such as SDA, described in Walker et al. 1992, Nucleic Acids Res. 20(7):1691-6, 1992, and rolling circle amplification, described in U.S. Pat. No. 5,648,245. Other amplification methods that may be used are described in U.S. Pat. Nos. 5,242,794, 5,494,810, 4,988,617 and in U.S. Ser. No. 09/854,317, U.S. Pat. Nos. 8,673,560 and 8,728,728 and US Pub. No. 20030143599, each of which is incorporated herein by reference. In some embodiments, DNA is amplified by multiplex locus-specific PCR. For example, the DNA can be amplified using Thermo Fisher's AmpliSeq® products. In one embodiment, the DNA is amplified using adaptor-ligation and single primer PCR. Other available methods of amplification, such as balanced PCR (Makrigiorgos, et al. (2002), *Nat Biotechnol,* Vol. 20, pp. 936-9), may also be used.

After the amplification step is complete, the first amplified product composition and the second amplified product composition, in embodiments where the nucleic acid sample was split into two channels for separate allele detection, can be combined to form an amplified product mixture comprising first amplified products and second amplified products. The first and second amplified products are then ready for hybridizing and labelling. In some embodiments, the amplified product compositions that undergo hybridization and labeling steps can be analyzed via array-based detection. Alternatively, the amplified product compositions can be processed by other techniques such as conventional or massively parallel sequencing. Thus, in some embodiments, the amplified product compositions, which can be optionally cleaved as described below, proceed to sequencing-based detection. The sequencing can be done via various methods available in the field, e.g., methods involving incorporating one or more chain-terminating nucleotides, e.g., Sanger Sequencing method that can be performed by, e.g., SeqStudio® Genetic Analyzer from Applied Biosystems. In other embodiments, the sequencing can include performing a Next Generation Sequencing (NGS) method, e.g., primer extension followed by semiconductor-based detection (e.g., Ion Torrent™ systems from Thermo Fisher Scientific) or via fluorescent detection (e.g., Illumina systems).

In some embodiments, after the amplification is complete, the amplified product compositions can be cleaved with one or more enzymes. In some embodiments, the amplified product compositions, e.g., the first and/or second amplified product compositions have a restriction enzyme recognition site. In some embodiments, the step of cleaving can be catalyzed by adding a restriction enzyme to the amplified product compositions, and in some embodiments, the first and second amplified product compositions. Suitable restriction enzymes include, but are not limited to AatII, Acc65I, AccI, AclI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BscRI, BscYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EacI, EagI, EarI, EciL, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinPII, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspAlI, MspI, MwoI, NaeI, Narf, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, Taqαl, TfiI, TliI, TseI, Tsp45I, Tsp509I, TspMI, TspRI, Tth111I, XbaI, XcmI, XhoI, XmaI, XmnI, and ZraI. In some embodiments, the restriction enzyme used to cleave the first and second amplified product compositions are identical or different. In some embodiments where the same restriction enzyme is used to cleave the first and second amplified product compositions, the restriction enzyme HaeIII is used to cleave its specific site present in the first and second amplified products. It will be appreciated that the amplified product composition which contains amplified MIP probes of the disclosure can be designed to contain one or more restriction sites. In the case where MIPs are designed with two or more restriction sites, one of skill in the art will understand how to design the MIPs such that the restriction enzymes will act selectively on each cleavage site of the MIP. In some embodiments, the cleavage of the amplified product compositions occur before or after combining the first and second amplified product compositions to form an amplified product mixture.

Detecting

The step of hybridizing at least one nucleic acid fragment containing or derived from the nucleic acid population and containing the polymorphic site to an oligonucleotide probe of an oligonucleotide array can be accomplished according to any known method in the art, and specifically in connection with the instructions received with any platform useful in connection with the present disclosure, such as the Axiom 2.0 reagent kit.

In some embodiments, the step of hybridization further includes a step of fixing. The fixing can include contacting the oligonucleotide array with nucleic acid hybridized thereto with a suitable fixing agent. In some embodiments, the fixing step occurs after the hybridization step is completed. In some embodiments, the fixing step occurs well after the hybridization step, e.g., after the hybridized array is washed and stained with a strain mixture. Therefore, in some embodiments, the array may undergo the steps of hybridization, washing, staining and fixing in this order, along with other steps.

The different primer pair amplified sequences can be differentiated based on spectrally distinguishable probes (e.g. 2 different dye-labeled probes such as Taqman or Locked Nucleic Acid Probes (Universal Probe Library, Roche)). In such approach, all probes are combined into a single reaction volume and distinguished based on the differences in the color emitted by each probe. For example, the probes targeting one polynucleotide (e.g., a test chromosome, such as chromosome 21) may be conjugated to a dye with a first color and the probes targeting a second polynucleotide (e.g., a reference chromosome, such as chromosome 1) in the reaction may be conjugated to a dye of a second color. The ratio of the colors then reflects the ratio between the test and the reference chromosome.

Illustratively, the first and second amplified product compositions comprise a nucleic acid sequence that, in some embodiments, corresponds to a channel composition. As an example, the amplified product composition from the first channel may comprise a first nucleic acid sequence and the amplified product compositions from the second channel may comprise a second nucleic acid sequence. Illustratively, the first and second nucleic acid sequences can bind or hybridize different agents for measuring the amount of the amplified product. In some embodiments, the amplified product compositions are directly labeled and measured.

The first and second amplified product compositions can be recombined and detected on a single array or can be kept separate and detected on at least 2 separate arrays. In embodiments where a single array is used, each of the first and second amplified product compositions can be labeled with a different reporter to allow for first and second product composition identification on the array. In embodiments where at least 2 arrays are used, the first and second amplified product compositions can be labeled with the same or different reporters. Exemplary single-channel systems include the Affymetrix "Gene Chip," the Illumina "Bead Chip," Agilent single-channel arrays, the Applied Microarrays "CodeLink" arrays, and the Eppendorf "Dual-Chip & Silverquant."

Amplified product composition hybridization to the array can be detected a variety of ways, including the direct or indirect attachment of fluorescent moieties, colorimetric moieties, chemiluminescent moieties, and the like. In some embodiments, probe-target hybridization can detected and quantified by detecting fluorophore-, radio-, silver-, or chemiluminescence-labeled agents to determine relative abundance of nucleic acid sequences in the target. In some embodiments, the amplified product composition is directly labeled with a fluorophore-, radio-, silver-, or chemiluminescence-label. Many comprehensive reviews of methodologies for labeling DNA provide guidance applicable to generating labeled oligonucleotide tags of the present invention. Such reviews include Haugland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); Wetmur, Critical Reviews in Biochemistry and Molecular Biology, 26: 227-259 (1991); Fung et al, U.S. Pat. No. 4,757,141; Hobbs, Jr., et al U.S. Pat. No. 5,151,507; Cruickshank, U.S.

Pat. No. 5,091,519. In some embodiments, one or more fluorescent dyes can be used labels. Some exemplary dyes are described by Menchen et al, U.S. Pat. No. 5,188,934 (4,7-dichlorofluorscein dyes); Begot et al, U.S. Pat. No. 5,366,860 (spectrally resolvable rhodamine dyes); Lee et al, U.S. Pat. No. 5,847,162 (4,7-dichlororhodamine dyes); Khanna et al, U.S. Pat. No. 4,318,846 (ether-substituted fluorescein dyes); Lee et al, U.S. Pat. No. 5,800,996 (energy transfer dyes); Lee et al, U.S. Pat. No. 5,066,580 (xanthene dyes): Mathies et al, U.S. Pat. No. 5,688,648 (energy transfer dyes); Maceivicz (U.S. Pat. Application No. 2005/0250147); Faham et al. (U.S. Pat. No. 7,208,295); and the like.

Possible methods of detection include direct detection of a reporter. In some embodiments, a complementary oligonucleotide to an amplified product composition comprises either a fluorescent/luminescent/chromogenic label or can be subsequently be reacted with additional compounds (e.g., immunostaining, aptamers) to generate a signal. In some embodiments, instead of hapten-labeled probes for detection, the labeling probes can have fluorophores conjugated directly which would eliminate the antibody-mediated signal amplification.

As described herein, an amplified product composition can be generated from PCR by primers flanking the markers. These amplicons can be produced singly or in multiplexed reactions. In some embodiments, amplified product compositions can be produced as ss-DNA by asymmetric PCR from one primer flanking the polymorphism or as RNA transcribed in vitro from promoters linked to the primers. As an example, a fluorescent label can be introduced into amplified product compositions directly as dye-bearing nucleotides or bound after amplification using dye-streptavidin complexes to incorporated biotin containing nucleotides. Illustratively, for amplified product compositions produced by asymmetric PCR, the reporter (e.g. a fluorescent dye) can be linked directly to the 5' end of the primer. In some embodiments, amplified product compositions can be labeled at the 3' end using TdT and a biotinylated dATP. Illustratively, this could be done for each of the separate gap fill reactions. In some embodiments, the 3' labeling using TdT and a biotinylated ATP leads to a one color, two chip read out.

The amplified product composition is hybridized to the array prior to or during labeling directly or indirectly with a detection agent. After or during the step of hybridization, a first agent that binds the first nucleic acid sequence of the amplified product compositions can be introduced. The first agent can be configured to bind to the first nucleic acid sequence present in the amplified products from the first channel. In some embodiments, the first agent comprises a complementary sequence to a portion of the first target sequence (e.g. the first nucleic acid sequence).

Illustratively, the first and second amplified product compositions comprise a nucleic acid sequence that, in some embodiments, corresponds to a channel composition. As an example, the amplified product composition from the first channel may comprise a first nucleic acid sequence and the amplified product compositions from the second channel may comprise a second nucleic acid sequence.

After or during the step of hybridization, a first agent that binds the first nucleic acid sequence of the amplified product compositions can be introduced. The first agent can be configured to bind to the first nucleic acid sequence present in the amplified products from the first channel. In some embodiments, the first agent comprises a complementary sequence to a portion of the first target sequence (e.g. the first nucleic acid sequence).

In some embodiments, the first agent comprises the first complementary sequence and a first recognition element conjugated to the first complementary sequence. Illustrative examples of first recognition elements include fluorophores, biotin, peptide tags, combinations thereof, or any known acceptable recognition element known in the art. In some examples, the first agent comprises biotin conjugated to the first complementary sequence.

Figure 4:
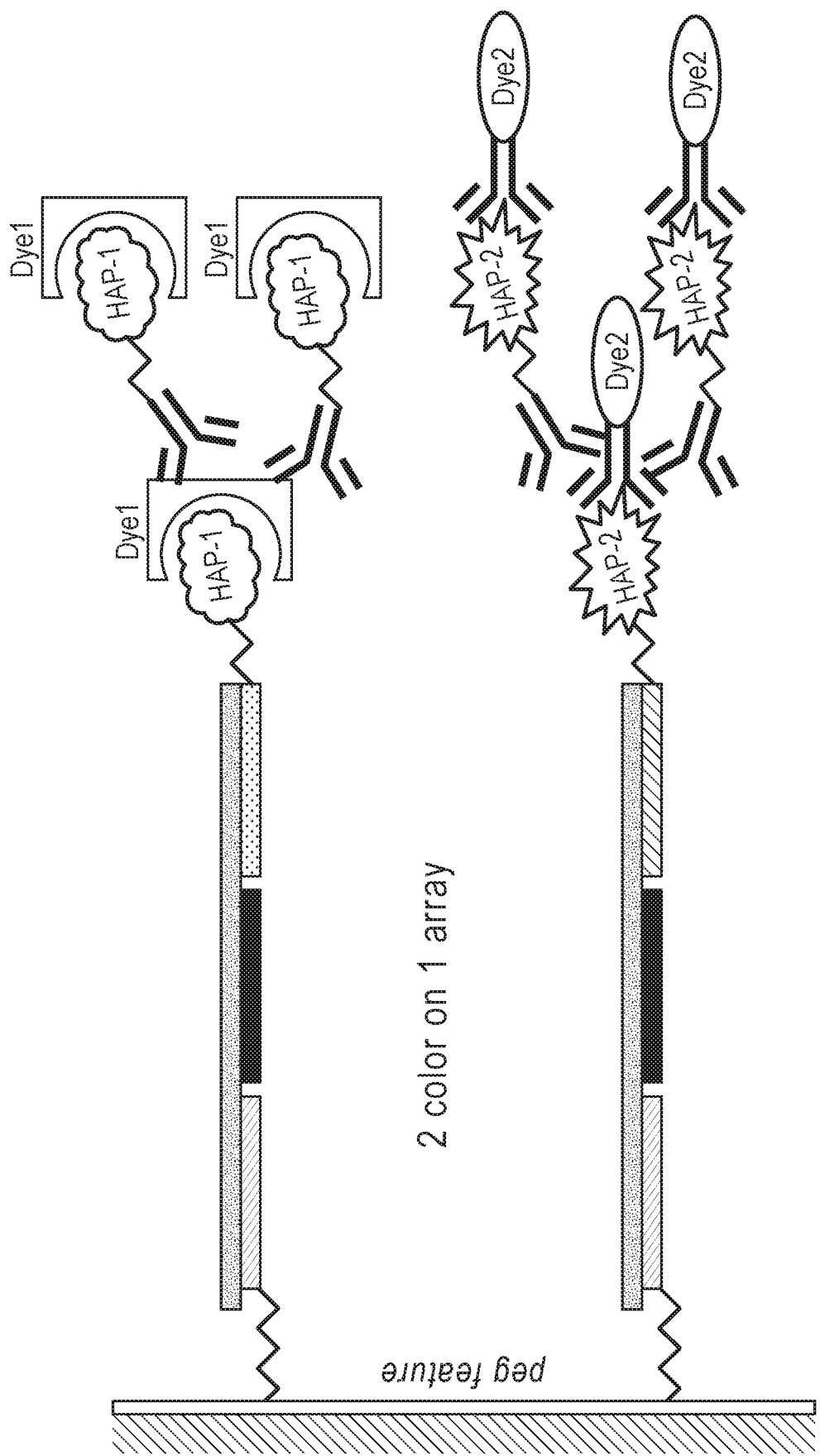
FIG. 4 is a diagrammatic view of hybridizing and staining the amplified product shown in FIG. 3 using an oligonucleotide array, showing the amplified product hybridized to a probe on the oligonucleotide array, and further showing detecting the hybridized product with either a first or second dye.

The first agent can further comprise a first reporter-labeled conjugate that binds to the first recognition element, as shown in FIG. 4. The first reporter-labeled conjugate may be an avidin, an antibody, an aptamer, combinations thereof, or any known acceptable conjugate that binds the recognition element. In some embodiments, the first reporter-labeled conjugate can be labeled with a first reporter. In some embodiments, the first reporter is a fluorophore.

In some embodiments, the first agent can further comprise a first conjugate antibody, as shown in FIG. 4. In illustrative embodiments, the first conjugate antibody binds to the first reporter-labeled conjugate. In some embodiments, the first conjugate antibody comprises a recognition element. In some embodiments, the recognition element of the first conjugate antibody can be the same as the first recognition element. In some examples, the first conjugate antibody can be labeled with biotin.

In some embodiments, the first reporter-labeled conjugate binds the recognition element conjugated to the first complementary sequence, the first conjugate antibody, or both the recognition element conjugated to the first complementary sequence and the first conjugate antibody, as shown in FIG. 4. In some embodiments, the first reporter-labeled conjugate binds both the recognition element conjugated to the first complementary sequence and the first conjugate antibody, each of the first reporter labeled conjugates comprises the same first reporter.

The first reporter may be a fluorophore, an enzymatic tag such as an HRP, a radioisotope, a combination thereof, or any suitable reporter typically used in biochemical assays, as shown in FIG. 4. In some embodiments, the fluorophore can have an emission peak between about 640 nm and about 680 nm. In some embodiments, the fluorophore is allophycocyanin.

After or during the step of hybridization, a second agent that binds the first nucleic acid sequence of the amplified product compositions can be introduced, as shown in FIG. 4. In some embodiments, the second agent comprises a complementary sequence to a portion of the second target sequence (e.g. the second nucleic acid sequence).

In some embodiments, the second agent comprises the second complementary sequence and a second recognition element conjugated to the second complementary sequence, as shown in FIG. 4. Illustrative examples of second recognition elements include fluorophores, biotin, peptide tags, combinations thereof, or any known acceptable recognition element known in the art. In some embodiments, the second agent comprises a fluorophore conjugated to the second complementary sequence. In some embodiments, the fluorophore can be FAM.

The second agent can further comprise a second reporter-labeled conjugate that binds to the second recognition element, as shown in FIG. 4. The second reporter-labeled conjugate may comprise an avidin, an antibody, an aptamer, combinations thereof, or any known acceptable conjugate that binds the recognition element. In some embodiments, the second reporter-labeled conjugate comprises an antibody. In some embodiments, the second reporter-labeled conjugate can be labeled with a second reporter. In some embodiments, the second reporter is a fluorophore.

In some embodiments, the second agent can further comprise a second conjugate antibody, as shown in FIG. 4. In illustrative embodiments, the second conjugate antibody binds to the second reporter-labeled conjugate. In some embodiments, the second conjugate antibody comprises a recognition element. In some examples, the recognition element of the second conjugate antibody can be the same as the second recognition element. In some examples, the second conjugate antibody can be labeled with FAM.

In some embodiments, the second reporter-labeled conjugate binds the recognition element conjugated to the second complementary sequence, the second conjugate antibody, or both the recognition element conjugated to the second complementary sequence and the second conjugate antibody, as shown in FIG. 4. In some embodiments, the second reporter-labeled conjugate binds both the recognition element conjugated to the second complementary sequence and the second conjugate antibody, each of the second reporter labeled conjugates comprises the same second reporter.

The second reporter may be a fluorophore, an enzymatic tag such as an HRP, a radioisotope, a combination thereof, or any suitable reporter typically used in biochemical assays, as shown in FIG. 4. In some embodiments, the fluorophore can have an emission peak between about 560 nm and about 600 nm. In some embodiments, the fluorophore is phycoerythin.

It will be appreciated that in some embodiments, the first agent can be configured to bind the amplified product compositions derived from the first channel and the second agent can be configured to bind the amplified product compositions of the second channel. It should be equally appreciated that in some embodiments, the first agent can be configured to bind the amplified product compositions derived from the second channel and the second agent can be configured to bind the amplified product compositions of the first channel. Accordingly, in some embodiments, the reporters (e.g. the fluorophore(s)) of the first agent are different than the reporters (e.g. the fluorophore(s)) of the second agent, as shown in FIG. 4.

In some embodiments, a set of probes (e.g., a set of probes targeting a test chromosome, e.g., Chromosome 21), may target different regions of a target polynucleotide, yet each probe within the set has the same universal primer-binding sites. In some cases, each probe has the same probe-binding site. In some cases, two or more probes in the reaction may have different probe-binding sites. In some cases, the probes added to such reactions are conjugated to the identical signal agent (e.g., fluorophores of the same color). In some cases, different signal agents (e.g., two different colors) are conjugated to one or more probes.

The oligonucleotide probe may also comprise a sequence that is complementary to a probe attached to a marker, such as a dye or fluorescent dye (e.g., TaqMan probe). In some cases, the TaqMan probe is bound to one type of dye (e.g., FAM, VIC, TAMRA, ROX). In other cases, there are more than one TaqMan probe sites on the oligonucleotide, with each site capable of binding to a different TaqMan probe (e.g., a TaqMan probe with a different type of dye). There may also be multiple TaqMan probe sites with the same sequence of the oligonucleotide probe described herein. Often, the TaqMan probe may bind only to a site on the oligonucleotide probe described herein, and not to genomic DNA, but in some cases a TaqMan probe may bind genomic DNA.

Analysis

In some embodiments, the disclosed methods (as well as relating compositions, systems, instruments and software) include a step of analyzing the data obtained from the array to analyze the properties of the nucleic acid sample (or derivative thereof) that is applied to the array. In some embodiments, the nucleic acid sample includes a mixed nucleic acid population containing a major subpopulation and a minor subpopulation.

In some embodiments, the disclosed methods can include detecting one or more signals from the oligonucleotide array using a detector.

Optionally, the detecting includes detecting a signal ("first signal" or "A signal") indicating the presence or absence of a first nucleotide variant. The first nucleotide variant optionally corresponds to a first allelic variant.

Optionally, the detecting includes detecting a signal ("second signal" or "B signal") indicating the presence or absence of a second nucleotide variant. The second nucleotide variant optionally corresponds to a second allelic variant.

In some embodiments, the disclosed methods can include determining the copy number of the first chromosomal region in the minor subpopulation using the first signal and the second signal.

In some embodiments, the disclosed methods can include determining the copy number of the first chromosomal region in the major subpopulation using the first signal and the second signal.

In some embodiments, the disclosed methods can include determining the genotype of the polymorphic site for the minor subpopulation using the first signal and the second signal.

In some embodiments, the disclosed methods can include determining the genotype of the polymorphic site for the major subpopulation using the first signal and the second signal.

In some embodiments, the disclosed methods can include determining the relative amounts of the major subpopulation and the minor subpopulation in the mixed nucleic acid population using the first signal and the second signal.

In some embodiments, the methods can include calculating the ratio of the first signal to the second signal, or the log ratio of the signals.

In some embodiments, the methods include analyzing the A signal and the B signal from an array feature configured to hybridize to a target nucleic acid containing a polymorphic site, and using the A signal and the B signal to determine both the genotype of the polymorphic site within the major and the minor subpopulations, as well as the copy number (or relative copy number) of the polymorphic site within the major and minor subpopulations.

Kits

Kits for performing the disclosed methods are also disclosed. The kits may comprise pools of molecular inversion probes designed for amplification of a plurality of target sequences. The target sequences are selected so that they each contain a polymorphic site of interest. The molecular inversion probes may be pooled into containers that contain 2 or more different sequence capture probes. The kit may further comprise adaptors, universal primers, dNTPs, ligase, buffer, and polymerase.

The kits may be used to amplify a collection of target sequences Amplification may be by fragmentation of the sample, ligation of an adaptor to the fragments, hybridization of capture probes to the adaptor-ligated fragments, extension of the capture probe, and amplification of the extended capture probes using a pair of universal primers.

The kits may also include a computer system for reading and analyzing mircoarray data. In addition, the kits may include a microarray chip for hybridizing and labeling the target sequences.

Applications

The methods and systems described herein can be used to detect genetic abnormalities of numerous types that are indicative of the presence of a disease or the possibility of developing a disease. For example, as described herein, the present disclosure can be useful for detecting copy number variants in a maternal sample that includes a major subpopulation and a minor subpopulation, wherein the major and minor subpopulations each include a target sequence located in a first chromosomal region and containing a polymorphic site. In some embodiments, the major population is maternal DNA. In some embodiments, the minor population is fetal DNA. In some embodiments, the fetal DNA is no greater than 15% of total DNA in the nucleic acid sample, or no greater than 10% of total DNA in the nucleic acid sample, or no greater than 5% of total DNA in the nucleic acid sample. In some embodiments, the major subpopulation is genotyped according to the methods described herein. In some embodiments, the minor subpopulation is genotyped according to the methods described herein.

In some embodiments, a sample includes a mixed nucleic acid population from different subpopulations (e.g., major and minor subpopulations). In one embodiment, a sample contains a mixture of maternal nucleic acids (a major subpopulation) and fetal nucleic acids (a minor subpopulation.) In one embodiments, the nucleic acids from each subpopulation are cell-free DNA. In some embodiments, the amount of the fetal DNA in a sample ranges from about 1% to about 50% of the total amount of DNA in the sample. In some embodiments, the amount of the fetal DNA in the sample is about 1%, about 5%, about 10%, about 15%, about 20%, about 25%, about 30%, about 35%, about 40%, about 45% or about 50% of the total amount of DNA in the sample, or any intervening amount of the foregoing. In some embodiments, the amount of the fetal DNA in the sample is no greater than about 1%, about 5%, about 10%, about 15%, about 20%, about 25%, about 30%, about 35%, about 40%, about 45% or about 50% of the total amount of DNA in the sample, or any intervening amount of the foregoing. In some embodiments, the amount of the fetal DNA in the sample is more or no less than about 1%, about 5%, about 10%, about 15%, about 20%, about 25%, about 30%, about 35%, about 40%, about 45% or about 50% of the total amount of DNA in the sample, or any intervening amount of the foregoing.

In some embodiments, the mixed nucleic acid population in a sample that can be processed according to various methods disclosed herein includes cell-free DNA from major and minor sources. In some embodiments, the mixed nucleic acid population is circulating DNA isolated from whole blood, plasma, serum or some other bodily fluid. In some embodiments, the mixed nucleic acid population includes maternal and fetal cell-free DNA. In some embodiments, the amount of mixed nucleic acid population in a sample is in the range from one or more nanograms (ngs) to about one or more milligrams (mgs). In some embodiments, the amount mixed nucleic acid population is about 1 ng, about 3 ngs, about 5 ngs, about 10 ngs, about 15 ngs, about 30 ngs, about 40 ngs, about 50 ngs, about 100 ngs, about 150 ngs, about 300 ngs, about 400 ngs, about 500 ngs, about 1 mg, about 3 mgs, about 5 mgs or more, or any intervening amount of the foregoing. In some embodiments, the amount of the mixed nucleic acid population used is no greater than about 50 ngs, about 40 ngs, about 30 ngs, about 15 ngs, about 10 ngs, about 5 ngs, about 3 ngs or about 1 ng. In some embodiments, the amount mixed nucleic acid population is about or less than about 50 ngs, about 40 ngs, about 30 ngs, about 15 ngs, about 10 ngs, about 5 ngs, about 3 ngs or about 1 ng.

In some embodiments, a sample that is processed according to various methods disclosed herein includes a mixed nucleic acid population derived from one or more of whole blood, plasma, serum, urine, stool or saliva. In some embodiments, a mixed nucleic acid population can be derived from blood. In some embodiments, blood, e.g., whole blood can be further processed to provide plasma and/or serum from which a mixed nucleic acid population for a sample is prepared.

In some embodiments, the disclosed methods (as well as related compositions, kits and systems) are useful in detecting genetic changes in small amounts of whole blood, plasma, serum or other bodily fluid. For example, the amount of bodily fluid (e.g., whole blood, plasma, serum or saliva) that is used to prepare a mixed nucleic acid population of a sample can be in the range of about 0.1 to several milliliters (mls). In some embodiments, the amount of whole blood, plasma, serum or other bodily fluid that is used to prepare a mixed nucleic acid population is about 0.1 ml, about 0.25 ml, about 0.5 ml, about 0.75 ml, about 1 ml, about 1.5 ml, about 2 mls, about 2.5 mls, about 3 mls, about 3.5 mls, about 4 mls, about 4.5 mls, about 5 mls about 5.5 mls, about 6 mls, about 6.5 mls, about 7 mls, about 7.5 mls, about 8 mls, about 8.5 mls, about 9 mls, about 9.5 mls, or about 10 mls, or any intervening volumes of the foregoing.

In some embodiments where whole blood is used to provide a mixed nucleic acid population of a sample, the amount of blood is about or less than 0.1 ml, 0.25 ml, about 0.5 ml, about 0.75 ml, about 1 ml, about 1.5 ml, about 2 mls, about 2.5 mls or about 3 mls. In some embodiments, the amount of blood is no greater than about 0.25 ml, about 0.5 ml, about 0.75 ml, about 1 ml, about 1.5 ml, about 2 mls, about 2.5 mls or about 3 mls.

In some embodiments where plasma or serum is used to provide a mixed nucleic acid population of a sample, the amount of plasma or serum is about or less than 0.1 ml, 0.25 ml, about 0.5 ml, about 0.75 ml, about 1 ml, about 1.5 ml, about 2 mls, about 2.5 mls or about 3 mls. In some embodiments, the amount of plasma or serum is no greater than about 0.25 ml, about 0.5 ml, about 0.75 ml, about 1 ml, about 1.5 ml, about 2 mls, about 2.5 mls or about 3 mls.

The methods and systems described herein can also be used to detect circulating tumor cells from a biological sample, e.g. blood that contains a major subpopulation and a minor subpopulation, wherein the major and minor subpopulations each include a target sequence located in a first chromosomal region and containing a polymorphic site. In some embodiments, the minor subpopulation can be genotyped to identify a known genetic marker for cancer, such as a SNP, a chromosomal inversion, a chromosomal deletion, a chromosomal insertion, and the like. It will be appreciated that numerous markers for cancer are known in the art.

EXAMPLES

Example 1: Annealing

Annealing was performed as generally described for the Oncoscan™ FFPE Assay kit (catalog #902293) available from Thermo Fisher.

Briefly, an assay microwell plate of 96 samples was prepared on ice. 10 μL of DNA was added to each well. The DNA sample may be an analytical gDNA sample (sheared to a median length of 170 bp); an analytical mixture of gDNA mixed with trisomy gDNA at 0, about 5%, or about 10% trisomy to analytical gDNA (sheared to a median length of 170 bp); or clinical cell-free DNA (cfDNA) purified from 10-20 mL maternal blood samples by MagMAX (available from Thermo Fisher) extraction kit methods.

An Anneal Master Mix (AMM) was prepared by mixing Buffer A of the Oncoscan™ FFPE Assay kit with a MIP probe mix containing about 48,000 MIPs from the OncoScan™ library. About 2.24 μL of AMM was added to each DNA sample and the reagents were mixed, vortexed, and centrifuged.

The microwell plate was placed in a thermocycler and incubated overnight according to the Oncoscan™ FFPE Assay protocol.

Example 2: Gap Filling and Channel Split

The gap filling was performed as generally described for the Oncoscan™ FFPE Assay.

Briefly, Buffer A, dNTPs, and the Cleavage Buffer were thawed on ice.

SAP recombinant enzyme was mixed with Buffer A and the Gap Fill Enzyme Mix. 2 μL of the prepared mixture was added to the microwell plate from Example 1. The contents of wells were then split equally into two new microwell plates to create two channels.

The microwell plates were placed in a thermocycler and incubated for 11 minutes using the Gap Fill program as described in the Oncoscan™ manual.

Example 3: dNTP Addition 2.4 μL of an ATP/TTP mix or a GTP/CTP were added to wells containing the DNA as described in Example 2. The microwell plates were placed back in a thermocycler to complete the Gap-Fill program.

Example 4: Exonuclease Treatment

An Exo Master Mix (EMM) was prepared by mixing the Exo Mix from the Oncoscan™ kit with glycerol and the wells were treated as described in the Oncoscan™ FFPE Assay.

Briefly, 2 μL of EMM was added and mixed with the solutions in the microwell plate from Example 3. The microwell plates were placed in a thermocycler and the program according to the Oncoscan™ FFPE Assay was continued.

Example 5: Cleavage and PCR

A Cleavage Master Mix (CMM) was prepared by mixing the Cleavage Buffer and Cleavage Enzyme according to the Oncoscan™ FFPE Assay. PCR mixes were prepared by mixing a complement mix (either A/T or C/G) with Titanium Taq (available from ClonTech).

15.0 μL of CMM was added to the wells of the microwell plate from Example 4 and mixed.

15.0 μL of the PCR mixes were added to the appropriate wells and mixed.

The microwell plates were placed in a thermocycler and incubated according to the Cleavage-PCR program as described in the Oncoscan™ FFPE Assay.

Example 6: Digestion

The digestion step was performed according to the Oncoscan™ FFPE Assay.

Briefly, Buffer B was thawed on ice. A HaeIII Master Mix (H3MM) was prepared by mixing Buffer B with HaeIII and the ExoI enzyme according to the Oncoscan™ FFPE Assay.

40 μL of H3MM was added to each sample well on a new microwell plate. To each filled well, 10 μL of an A/T product was mixed with 10 μL of a C/G product and mixed.

The plate was placed in a thermocycler and incubated using the HaeIII Digest program according to the Oncoscan™ FFPE Assay.

Example 7: Denaturation and Hybridization

The denaturation and hybridization were performed according to and with reagents from the Axiom 2.0 reagent kit (catalog #901758) available from Thermo Fisher.

Briefly, the Hybe Mix was thawed on ice and then 82.3 μL/well was pipetted into a microwell plate.

36 μL of the digested product from Example 6 was added to each well containing the Hybe Mix. The plate was incubated for 25 minutes at room temperature. The microwell plate was then incubated in a thermocycler at 95° C. for 10 minutes, then 49° C. for at least 3 minutes.

About 100 μL of the denatured product from each well was added to the Hybe tray from the Axiom 2.0 kit and the plate was placed in a GeneTitan™Multi-Channel (GTMC) instrument and incubated for 23.5 hours.

Example 8: Washing, Fixing, and Staining

The Hybe tray was washed and stained generally according to the Axiom 2.0 manual.

Briefly, a holding tray was prepared by adding 150 μL of the Axiom holding buffer into each well of a microwell plate. A stabilization/fixing solution was prepared according to the Axiom 2.0 manual and 150 μL of the solution was added into each well of a microwell plate.

A first stain mix was prepared according to the Axiom 2.0 manual and modified by using a polyclonal antibody and 105 μL of the solution was added into each well of two microwell plates.

A second stain mix was prepared according to the Axiom 2.0 manual and modified by using a polyclonal antibody and 105 μL of the solution was added into each well of a microwell plate.

The trays were added to the GTMC instrument. The GTMC instrument performed the washing, staining, fixing, and holding-filling according to the Axiom 2.0 manual.

Example 9: Collecting the Data

The stained tray from Example 8 was imaged according to the Axiom 2.0 protocol. The data was collected and analyzed.

What is claimed is:

1. A method for analyzing a mixed nucleic acid sample obtained from an organism, comprising:
   obtaining or deriving from an organism a nucleic acid sample containing a mixed nucleic acid population that includes a major subpopulation and a minor subpopulation, wherein the major and minor subpopulations each include a target sequence located in a first nucleic acid locus and containing a polymorphic site, wherein the polymorphic site can include combinations of a first nucleotide variant and a second nucleotide variant;
   genotyping the polymorphic site, wherein the genotyping includes:
   (a) contacting the nucleic acid sample with a pool of linear molecular inversion probes to provide an annealing mixture, wherein portions of the linear molecular inversion probes hybridize to the target sequence;
   (b) dividing the annealing mixture into a first channel composition and a second channel composition;
   (c) adding a mixture of deoxynucleotides to each of the first and second channel composition, wherein the mixture of deoxynucleotides added to the first channel composition is different from the mixture of deoxynucleotides added to the second channel composition;
   (d) contacting the first and second channel compositions with a ligase to form first and second circularized probe compositions from the linear molecular inversion probes;
   (e) cleaving the first and second circularized probe compositions to form first and second linearized probe compositions;
   (f) combining the first and second linearized probe compositions;
   (g) hybridizing the first and second linearized probe compositions to an oligonucleotide probe of an oligonucleotide array; and
   (h) detecting from the oligonucleotide array, using a detector, a first signal indicating the presence or absence of the first nucleotide variant ("A signal") corresponding to a first allelic variant and a second signal indicating the presence or absence of the second nucleotide variant ("B signal") corresponding to a second allelic variant.

2. The method of claim 1, further including determining a copy number of the first nucleic acid locus in the minor subpopulation, the major subpopulation, or both the major and minor subpopulations, using the first signal and the second signal.

3. The method of claim 1, further including determining a copy number of a chromosome containing the first nucleic acid locus in the major subpopulation, the minor subpopulation or both the major and minor subpopulations, using the first signal and the second signal.

4. The method of claim 1, further including determining a genotype of the polymorphic site for the minor subpopulation and/or the major subpopulation using the first signal and the second signal.

5. The method of claim 1, further including determining relative amounts of the major subpopulation and the minor subpopulation in the mixed nucleic acid population using the first signal and the second signal.

6. The method of claim 1, wherein the major subpopulation and the minor subpopulation originate from different sources in the organism.

7. The method of claim 1, wherein the mixed nucleic acid population includes cell-free DNA.

8. The method of claim 7, wherein the cell-free DNA is obtained or derived from blood, plasma, serum, urine, stool or saliva of the organism.

9. The method of claim 1, wherein the organism includes a tumor, the major subpopulation includes or is derived from normal tissue and the minor subpopulation includes or is derived from the tumor.

10. The method of claim 1, wherein the organism is a pregnant female, the mixed nucleic acid population is cell-free DNA obtained from blood of the pregnant female, the major subpopulation includes or is derived from maternal nucleic acid and the minor subpopulation includes or is derived from fetal nucleic acid.

11. The method of claim 1, wherein the polymorphic site includes a bi-allelic SNP, the first nucleotide variant is a first allelic variant of the SNP ("A allele") and the second nucleotide variant is a second allelic variant of the SNP ("B allele").

12. The method of claim 1, further comprising multiplex genotyping of multiple polymorphic sites, wherein at least 50% of the pool of linear molecular inversion probes are configured to target sequences of the mixed nucleic acid sample from chromosomes 1, 5, 13, 18, 21, X, and Y.

13. The method of claim 1, wherein the mixed nucleic acid sample comprises DNA fragment copies, and wherein a ratio of a total number of the linear molecular inversion probes to a total number of DNA fragment copies is at least 15,000:1.

14. The method of claim 1, wherein the step of genotyping further includes amplifying the first and second linearized probe compositions prior to hybridizing the first and second linearized probe compositions to the oligonucleotide probe of the oligonucleotide array.

15. The method of claim 1, wherein the step of detecting further includes, after the step of hybridizing the first and second linearized probe compositions to the oligonucleotide probe of the oligonucleotide array, labeling the first and second linearized probe compositions with a first agent that binds to the first linearized probe composition and a second agent that binds to the second linearized probe composition.

16. The method of claim 15, wherein the first agent comprises a complementary sequence to a portion of the first linearized probe composition.

17. The method of claim 15, wherein the second agent comprises a complementary sequence to a portion of the second linearized probe composition.

18. The method of claim 14, wherein the genotyping of the polymorphic site further comprises cleaving the first and second linearized probe compositions at one or more restriction enzyme recognition sites after amplifying of the first and second linearized probe compositions.

* * * * *